(12) United States Patent
Johnson

(10) Patent No.: US 12,274,612 B2
(45) Date of Patent: Apr. 15, 2025

(54) IMPLANTABLE INTRALUMINAL DEVICE

(71) Applicant: W. L. Gore & Associates, Inc., Newark, DE (US)

(72) Inventor: Matthew A. Johnson, Bear, DE (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 18/521,013

(22) Filed: Nov. 28, 2023

(65) Prior Publication Data

US 2024/0099828 A1 Mar. 28, 2024

Related U.S. Application Data

(63) Continuation of application No. 17/509,672, filed on Oct. 25, 2021, now Pat. No. 11,857,407, which is a continuation of application No. 16/528,069, filed on Jul. 31, 2019, now Pat. No. 11,166,806, which is a continuation of application No. 15/879,224, filed on Jan. 24, 2018, now Pat. No. 10,405,966, which is a continuation of application No. 14/152,545, filed on Jan. 10, 2014, now Pat. No. 9,907,641.

(60) Provisional application No. 61/748,881, filed on Jan. 4, 2013.

(51) Int. Cl.
*A61F 2/07* (2013.01)
*A61F 2/04* (2013.01)
*A61F 2/852* (2013.01)
*A61F 2/88* (2006.01)
*A61F 2/89* (2013.01)

(52) U.S. Cl.
CPC .................. *A61F 2/07* (2013.01); *A61F 2/04* (2013.01); *A61F 2002/041* (2013.01); *A61F 2002/075* (2013.01); *A61F 2/852* (2013.01); *A61F 2/88* (2013.01); *A61F 2/89* (2013.01); *A61F 2240/001* (2013.01); *A61F 2250/0065* (2013.01); *Y10T 29/49826* (2015.01)

(58) Field of Classification Search
CPC .... A61F 2/04; A61F 2/07; A61F 2/852; A61F 2/88; A61F 2/89; A61F 2002/041; A61F 2002/075; A61F 2240/001; A61F 2250/0065
See application file for complete search history.

(56) References Cited

U.S. PATENT DOCUMENTS

2006/0217796 A1* 9/2006 DiMatteo .................. A61F 2/06
 623/1.16
2007/0219612 A1* 9/2007 Andreas ........... A61B 17/12022
 623/1.11

* cited by examiner

*Primary Examiner* — Mohamed G Gabr

(57) ABSTRACT

This document provides implantable intraluminal stent graft medical devices. In some embodiments, the stent graft devices provided herein are implantable in bodily conduits that have side branches, and the stent graft devices are operable to allow the flow of fluids between the conduit and the side branches. In some embodiments, the walls of the stent graft devices provided herein include compliant channels which allow for fluid communication between the interior and the exterior of the stent graft devices. In some embodiments, the compliant channels are configured to inhibit or reduce tissue ingrowth, tissue bridging, and/or endothelialization.

20 Claims, 10 Drawing Sheets

IMPLANTABLE INTRALUMINAL DEVICE

CROSS-REFERENCE TO RELATED APPLICATION

This application is a continuation of U.S. Ser. No. 17/509,672, filed Oct. 25, 2021, which is a continuation of U.S. Ser. No. 16/528,069, filed Jul. 31, 2019, now U.S. Pat. No. 11,166,806, issued Nov. 9, 2021, which is a continuation of U.S. Ser. No. 15/879,224, filed Jan. 24, 2018, now U.S. Pat. No. 10,405,966, issued Sep. 10, 2019, which is a continuation of U.S. patent application Ser. No. 14/152,545, filed Jan. 10, 2014, now U.S. Pat. No. 9,907,641, issued Mar. 6, 2018, all of which are incorporated herein by reference in their entireties for all purposes.

TECHNICAL FIELD

This document relates to implantable intraluminal medical devices. For example, this document relates to stent graft devices that can be implanted in bodily cavities, organs, and vessels.

BACKGROUND

In numerous locations of the human anatomy, a primary conduit is connected with one or more secondary conduits that branch off from the primary conduit. In some cases the secondary branches conduct fluid into the primary conduit, while in other cases the secondary branches conduct fluid away from the primary conduit.

The human vasculature includes many examples of primary conduits that have secondary branches. One example of a primary conduit is the aorta. In the aortic arch region, three arteries branch off from the aorta. Those three arteries are the brachiocephalic artery, the left common carotid artery, and the left subclavian artery, and they conduct fluid away from the aorta.

The ductal system of the pancreas provides another example of a primary conduit with secondary branches. The main pancreatic duct receives enzymes that flow into the duct from the side branches.

The left and right intrahepatic ducts of the liver provide yet another example of primary conduits with secondary branches. The intrahepatic ducts receive bile that flows into the common hepatic duct Conduits within the human body can experience a variety of problems. For example, conduits can have strictures that cause the conduit to become occluded. In some cases, plaque or embolic material can create an occlusion. In the pancreas and liver, for example, stones and other conditions can occlude the pancreatic, bile, and hepatic ducts.

An aneurysm, another potential problematic condition associated with body conduits, is a weakening of the wall of a conduit that causes a bulge in the wall as a result of pressure within the conduit. The bulged wall may burst if the pressure is not relieved. For example, arteries such as the aortic arch can experience aneurysms.

Implantable stent graft devices can be used to treat various problems afflicting conduits. In general, a stent graft is a tubular device which is composed of a membrane supported by a frame. For example, stent grafts can be installed in the location of a stricture to create an open passageway for fluid flow. Stent grafts can also treat aneurysms by providing a conduit liner to relieve the pressure on the weakened wall of an aneurysm.

When stent grafts are installed in conduits that have branches, the membranous wall covering of the stent graft has the potential to block the fluid flow between the conduit and the branches. Therefore, provisions that allow fluid flow between a conduit containing a stent graft and the conduit's branches are desirable. For example, in some cases, stent grafts can include discrete flow path sites in the membranous wall covering of the stent graft (e.g., fenestrations, tubes, channels, etc.). The discrete flow paths are intended to be located in areas on the wall of the stent graft that are in alignment with the anastomoses of the branches. However, such alignment can be challenging to achieve on a consistent basis.

The anatomical configuration of conduit networks, such as the vasculature or the pancreatic, hepatic, and biliary ductal systems, can be unique in every person. That is, the branches from the primary conduits, or the bifurcation of two primary conduits, are likely to be in different locations, and be different sizes, from one person to the next.

SUMMARY

This document provides implantable intraluminal medical devices. For example, this document provides stent graft devices that can be implanted in bodily conduits. In some embodiments, the stent graft devices provided herein are implantable in bodily conduits that have side branches, and the stent graft devices are operable to allow the flow of fluids between the conduit and the side branches.

In general, one aspect of this document features an implantable intraluminal device with resistance to tissue ingrowth. The device comprises a tubular member defining a lumen having an inner surface, an outer surface and a wall extending therebetween defined by a plurality of spaced apart circumferential support elements. The device also comprises a covering disposed on at least one of the surfaces of the tubular member. The covering includes a plurality of compliant channels therein, with a first opening, a length, and a second opening. At least the first opening of the compliant channels is located between the spaced apart support elements. The length of the compliant channels is sufficient to impede tissue ingrowth.

In various implementations, the length of the compliant channels of the implantable intraluminal device may be greater than about 2 mm. The length of the compliant channels of the implantable intraluminal device may be greater than about 5 mm. The length of the compliant channels of the implantable intraluminal device may be greater than about 10 mm.

In a second general aspect, a tubular intraluminal device comprises a main body defining a lumen. The main body comprises an inner surface, an outer surface, and a wall extending therebetween. The wall is defined by at least two circumferential support elements that are spaced longitudinally apart at a first predetermined length. The device also comprises at least a first biocompatible flexible membrane disposed on a surface of the tubular member, wherein the membrane has a proximal edge fixed to a first proximal support element and a free distal edge extending longitudinally to a second predetermined length. The second predetermined length is greater than said first predetermined length. The flexible membrane defines a compliant channel which allows for fluid communication between the inner surface and the outer surface of the main body.

In various implementations, the free distal edge may be oriented to extend longitudinally within an inner circumference of an adjacent distal support element. The free distal edge may be oriented to extend longitudinally about the periphery of an adjacent distal support element. The spaced apart support elements may be independent ring-like stents. The spaced apart support elements may be individual windings of a helically wound wire.

In a third general aspect, an intraluminal stent graft with resistance to tissue ingrowth, which allows for fluid communication between a defined lumen and surrounding tissues at multiple points along its length comprises a helically wound wire. The stent graft also comprises at least one biocompatible flexible tape material having a first edge, a second edge and a distance therebetween. The first edge of the tape material is fixed to at least a first proximal winding of the helically wound wire and the second edge of the tape material is oriented to extend through an inner circumference of at least one distal adjacent winding of the helically wound wire.

In a fourth general aspect, an implantable intraluminal device comprises an elongate tubular member with a longitudinal axis. The elongate tubular member comprises a plurality of discrete substantially cylindrical segments, wherein each cylindrical segment comprises a substantially cylindrical membranous wall with first and second open ends and one or more annular reinforcement members fixedly attached to the membranous wall. Each cylindrical segment has an axis, and the cylindrical segments are arranged adjacently such that a combination of the axes of the cylindrical segments coincide with the longitudinal axis of the elongate tubular member, and the membranous walls of adjacent cylindrical segments longitudinally overlap by a distance. The device also comprises an elongate axial reinforcement member. The elongate axial reinforcement member is fixedly attached to each of the cylindrical segments.

In various implementations, the annular reinforcement members may have a width measured in a direction parallel to the longitudinal axis of the elongate tubular member, and the distance of the overlap may be greater than the width of the reinforcement members.

In a fifth general aspect, an implantable medical device comprises an elongate tubular member with a longitudinal axis. The elongate tubular member comprises a helically arranged membranous strip and a helically arranged support member fixedly attached to the helically arranged membranous strip. The helically arranged membranous strip and the helically arranged support member comprise a plurality of turns. The membranous strip has first and second side regions along opposite lengthwise sides. The first and second side regions that correspond to adjacent turns overlap by a distance. The device also comprises an elongate axial reinforcement member. The elongate axial reinforcement member is fixedly attached to each of the plurality of turns.

In a sixth general aspect, a method for fabricating a stent graft device comprises arranging a membranous material on a mandrel; attaching a plurality of annular support members onto the membranous material; cutting the membranous material to create a plurality of discrete substantially cylindrical segments, wherein each cylindrical segment comprises a substantially cylindrical membranous wall with first and second open ends and one or more annular support members attached to the membranous wall; arranging the plurality of cylindrical segments so that the membranous walls of adjacent cylindrical segments longitudinally overlap by a distance; and applying one or more elongate axial reinforcement members, wherein the one or more elongate axial reinforcement members are fixedly attached to each of the cylindrical segments.

In a seventh general aspect, a method for fabricating a stent graft device comprises arranging a membranous material on a mandrel; attaching a helically arranged support member onto the membranous material; cutting the membranous material along an edge of the helically arranged support member to create a helical membranous strip, wherein the helical membranous strip comprises a plurality of turns, and wherein the helical membranous strip has first and second side regions along opposite lengthwise sides; arranging the helical membranous strip to comprise a plurality of turns, wherein the first and second side regions that correspond to adjacent turns overlap by a distance; and applying one or more elongate axial reinforcement members, wherein the one or more elongate axial reinforcement member are fixedly attached to each of the turns.

In an eighth general aspect, a method for fabricating a stent graft device comprises providing a plurality of discrete substantially cylindrical segments, wherein each cylindrical segment comprises a substantially cylindrical membranous wall with first and second open ends and one or more annular support members attached to the membranous wall; arranging the plurality of cylindrical segments so that the membranous walls of adjacent cylindrical segments longitudinally overlap by a distance; and applying one or more elongate axial reinforcement members, wherein the one or more elongate axial reinforcement members are fixedly attached to each of the cylindrical segments.

In a ninth general aspect, a method of using a stent graft device to treat a human comprises providing a stent graft device. The stent graft device comprises an elongate tubular member with a longitudinal axis. The elongate tubular member comprises a plurality of discrete substantially cylindrical segments. Each cylindrical segment comprises a substantially cylindrical membranous wall with first and second open ends and one or more annular reinforcement members fixedly attached to the membranous wall. Each cylindrical segment has an axis. The cylindrical segments are arranged adjacently such that a combination of the axes of the cylindrical segments coincide with the longitudinal axis of the elongate tubular member and the membranous walls of adjacent cylindrical segments longitudinally overlap by a distance. The stent graft device also comprises an elongate axial reinforcement member. The elongate axial reinforcement member is fixedly attached to each of the cylindrical segments. The method also comprises delivering the stent graft device to a treatment site in the human and implanting the stent graft device at the treatment site in the human.

In a tenth general aspect, a method of using a stent graft device to treat a human comprises providing a stent graft device. The stent graft device comprises a helically arranged membranous strip and a helically arranged support member fixedly attached to the helically arranged membranous strip. The helically arranged membranous strip and the helically arranged support member comprise a plurality of turns. The membranous strip has first and second side regions along opposite lengthwise sides. The first and second side regions that correspond to adjacent turns overlap by a distance. The stent graft device also comprises an elongate axial reinforcement member. The elongate axial reinforcement member is fixedly attached to each of the plurality of turn. The method also comprises delivering the stent graft device to a treatment site in the human and implanting the stent graft device at the treatment site in the human.

Particular embodiments of the subject matter described in this specification can be implemented so as to realize one or more of the following advantages. The stent graft devices provided herein are suitable for implantation in bodily conduits including conduits that have side branches. The stent graft devices can operably allow the flow of fluids between a conduit and side branches of the conduit. The stent graft devices can allow the flow of fluids between a conduit and one or more side branches along substantially the entire length of the stent graft device. The stent graft devices can allow the flow of fluids between a conduit and one or more side branches of the conduit without requiring alignment of portions of the stent graft device with the anastomoses of the side branches. In some embodiments, the stent grafts are configured to facilitate fluid flow from a conduit towards one or more side branches. In some embodiments, the stent grafts are configured to facilitate fluid flow from one or more side branches towards the conduit. In some embodiments, the stent graft devices provided herein are configured to inhibit tissue encapsulation, so as to facilitate removal of the device from the conduit after a period of time, and to prevent potential blockage of the conduit or side vessels caused by ingrowth. The stent grafts are configured to have greater structural integrity than stent grafts that facilitate flow between a conduit and side branches of the conduit by having a series of fenestrations in the wall of the stent graft.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This document provides implantable intraluminal medical devices. For example, this document provides stent graft devices that can be implanted in bodily conduits. In some embodiments, the stent graft devices provided herein are suited for implantation in bodily conduits that have side branches. In some embodiments, the stent graft devices provided herein operably allow the flow of fluids between the primary conduit and the side branches through flow channels disposed at the peripheral wall of the stent graft devices.

Figure 1A:
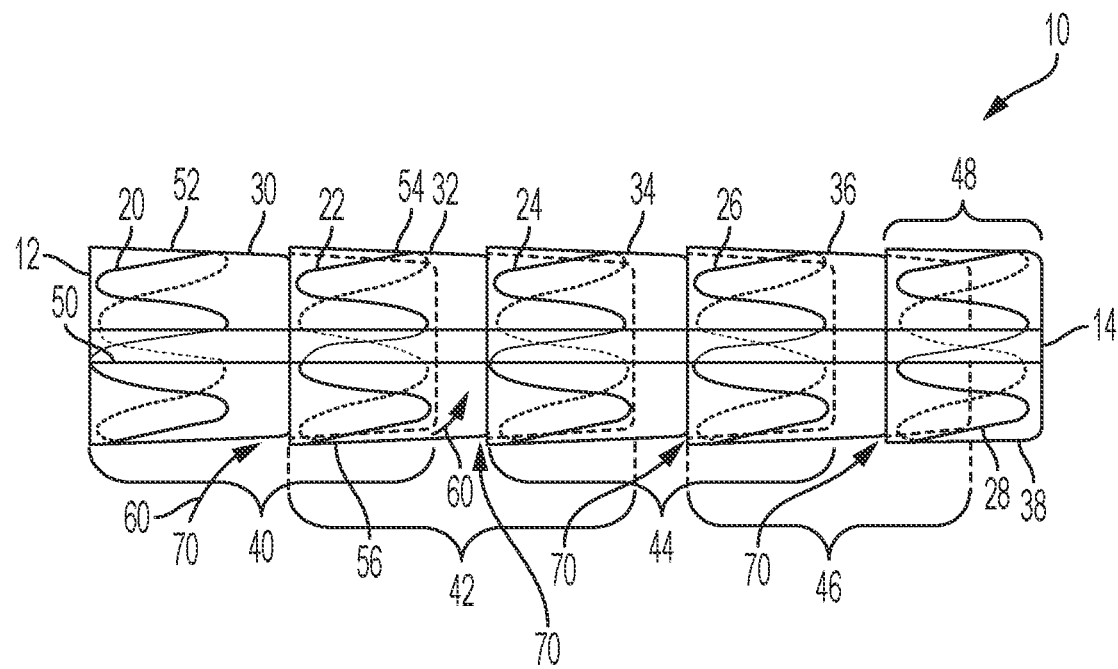
FIGS. 1A and 1B illustrate schematic side views of example embodiments of stent graft devices that can be deployed within a bodily conduit.

With reference to FIG. 1A, an example stent graft device 10 includes multiple tubular segments 40, 42, 44, 46, and 48. Each tubular segment 40, 42, 44, 46, and 48 includes an individual annular stent member 20, 22, 24, 26, and 28, respectively, and a tubular membrane 30, 32, 34, 36, and 38, respectively. Adjacent segments of the tubular segments 40, 42, 44, 46, and 48 are partially nested within each other and are connected to one another by one or more axial reinforcement members 50. While the example stent graft 10 is composed of five (5) tubular segments 40, 42, 44, 46, and 48, some embodiments of the stent graft devices provided herein have fewer than five (5) segments (e.g., four (4), three (3), or two (2)). Some embodiments of the stent graft devices provided herein have more than five (5) segments (e.g., six (6), seven (7), eight (8), nine (9), ten (10), or more). Stent graft devices having any appropriate number of segments are envisioned within the scope of this document.

Stent graft 10 includes a first end 12 and a second end 14. Stent graft 10 is configured to conduct fluid flow between the first end 12 and the second end 14. As used herein, fluid flow within the lumen of a stent graft and between the first and second ends of the stent graft may be referred to as "axial" flow.

Connecting the first end 12 and the second end 14 is a substantially cylindrical tunnel. The peripheral wall of the tunnel is defined by the annular stents 20, 22, 24, 26, and 28, and the tubular membranes 30, 32, 34, 36, and 38.

Stent graft device 10 is also configured to facilitate flow through the peripheral wall of stent graft device 10, from the exterior to the interior of stent graft device 10. Said differently, in some embodiments, stent graft device 10 is configured to facilitate inward radial flow.

As used herein, "radial" flow refers to any fluid flow between the exterior and interior of the stent graft that is conducted through flow channels 70 disposed at the peripheral wall of the stent grafts provided herein. Such radial flow is to be distinguished from axial flow as described above. While the term radial flow is used, it is not intended to be limiting in terms of the specific geometry or angle of the fluid flow path. That is, any flow between the interior and exterior (in either direction) through the peripheral wall of the stent grafts provided herein may be described herein as radial flow, even if a portion of such flow may be substantially parallel to the axis of the stent graft. The radial flow capabilities of the stent grafts provided herein can facilitate flow between one or more side branches and a primary conduit containing a stent graft, as will be described further below.

In some embodiments, axial reinforcement members can function like a "backbone" of the stent graft devices provided herein. That is, axial reinforcement members can help the stent graft maintain a desired physical configuration. For example, axial reinforcement member 50 links together segments 40, 42, 44, 46, and 48, and assists in defining the spacing between the segments. Axial reinforcement member 50 defines the overall length of example stent graft device 10.

In some embodiments, an axial reinforcement member is adhered to portions of the outer wall surface of the stent graft device. In some embodiments, an axial reinforcement member is adhered to the inner wall surface of the stent graft device. In some embodiments, an axial reinforcement member is adhered to both the inner and outer wall surfaces of the stent graft device. In some embodiments, the axial reinforcement members are strips of biocompatible membrane material that are adhered to portions of the stents and membranes of the segments. In some embodiments, other materials, such as metallic or polymeric wires, can be used for the axial reinforcement member.

In some embodiments, tubular membrane segments can be linked together by having discrete bondable areas on the tubular membranes 30, 32, 34, 36, and 38. The discrete bondable areas adhere portions of adjacent tubular membrane segments together. In those embodiments, an additional axial reinforcement member may not be needed. In some embodiments, a combination of discrete bondable areas and additional axial reinforcement members are used to link adjacent tubular membrane segments.

Axial reinforcement members can have any suitable width. For example, in some embodiments axial reinforcement members made from membranous material can be about ¼" wide. Membranous axial reinforcement members with any other suitable width are also envisioned. Any suitable quantity of axial reinforcement members can be included in a stent graft device. For example, in some embodiments, one (1) axial reinforcement member is included. In some embodiments, two (2) axial reinforcement members are included. In some embodiments, three (3) or more axial reinforcement members are included. In some implementations where more than one axial reinforcement member is used, the axial reinforcement members may be approximately equally spaced around a circumference of the device, for example. In some implementations where more than one axial reinforcement member is used, the axial reinforcement members are not equally spaced around a circumference of the device.

In some embodiments, the tubular membranes 30, 32, 34, 36, and 38 are comprised of a membranous material that inhibits or reduces passage of blood and other bodily fluids. In some embodiments, the tubular membranes 30, 32, 34, 36, and 38 have a material composition and configuration that inhibits or prevents tissue ingrowth to the membrane. In some embodiments, the tubular membranes 30, 32, 34, 36, and 38, or portions thereof, have a microporous structure that provides a tissue ingrowth scaffold for durable occlusion and supplemental anchoring strength of the stent graft device. Some embodiments of the tubular membranes 30, 32, 34, 36, and 38 comprise a fluoropolymer, such as an expanded polytetrafluoroethylene (ePTFE) polymer. In some embodiments, the tubular membranes 30, 32, 34, 36, and 38 comprise a polyester, a silicone, a urethane, or another biocompatible polymer, or combinations and subcombinations thereof. In some embodiments, the tubular membranes 30, 32, 34, 36, and 38 may be formed of a copolymer. In some embodiments, a first portion of the tubular membranes 30, 32, 34, 36, and 38 is formed of a first material and a second portion of the tubular membranes 30, 32, 34, 36, and 38 is formed of a second material. For example, the portion of the tubular membranes 30, 32, 34, 36, and 38 near the stent members 20, 22, 24, 26, and 28 may be formed of a first material, and the remainder of the tubular membranes 30, 32, 34, 36, and 38 may be formed of a second material. In some embodiments, portions of the membrane have one or more radiopaque markers attached thereto to enhance in vivo radiographic visualization.

In general, the stent members of a stent graft device provide a structural framework for the stent graft device. Whereas the membranous covering of a stent graft by itself may tend to be relatively flaccid, the stent members can provide desired structural strength and rigidity to the stent graft device. The stent members can provide structure that is useful during the deployment process. In general, the stent graft devices provided herein can be deployed using transcatheter techniques.

Stent members can be attached to membranous coverings in a variety of suitable manners well known to those of ordinary skill in the art. For example, in some embodiments, the stent members are sewn to the membranous covering. In some embodiments, the stent members are glued to the membranous covering. In some embodiments, the stent members are sandwiched between layers of membranous covering.

In some embodiments, portions of the stent members have one or more radiopaque markers attached thereto to enhance in vivo radiographic visualization. In some embodiments, the materials of the stent members themselves are constructed to enhance in vivo radiographic visualization of the stent members. For example, in some embodiments the stent members can be at least partially hollow and radiopaque material can be inserted within the hollow portions of the stent members.

In some embodiments, the stent members are self-expanding to thereby intrinsically provide radial force that can bear against the wall of a bodily lumen or cavity. Self-expanding stent members are often comprised of super elastic shape-memory Nitinol (NiTi) material. In some embodiments, a secondary device such as a balloon is used to provide a temporary supplemental radial force to help expand the stent members into contact with the wall of a bodily lumen or cavity and to expand a constricted area of the lumen or cavity. Such stent members may be comprised of stainless steel or other materials. Stent members can be fabricated in various manners, such as by forming a wire, or by laser cutting a tube, and the like. These and all other variations of stent member types, material compositions, material treatments, configurations, fabrication techniques, and methods for attaching stents to membranous coverings are envisioned and within the scope of the stent graft devices provided herein.

Stent members 20, 22, 24, 26, and 28 of example stent graft 10 are depicted as NiTi wire rings that have been heat-set into a sinusoidal wave pattern. Each segment, 40, 42, 44, 46, and 48 includes an individual stent member 20, 22, 24, 26, and 28, respectively.

With the exception of segment 48, which serves as a unique end segment, the stent members 20, 22, 24, and 26 are located asymmetrically in relation to the segmented tubular membranes 30, 32, 34, and 36. That is, stent members 20, 22, 24, and 26 are located off-center and nearer to one of the edges of their respective membranes 30, 32, 34, and 36. As a result of the asymmetrical location of the stent members 20, 22, 24, and 26, one end portion of each membrane 30, 32, 34, and 36 is supported by a stent member, while the other end portion of each membrane 30, 32, 34, and 36 is not supported by a stent member. Therefore, one end portion of each segment 40, 42, 44, and 46 is supported by a stent member, but the other end portion of each segment 40, 42, 44, and 46 is unsupported and relatively flaccid, compared to the supported end portion.

Segment 40 can be used to illustrate the previous point. Segment 40 includes a supported edge portion 52 and an unsupported edge portion 54. The supported edge portion 52 is supported by stent member 20, whereas the unsupported edge portion 54 has no such supplemental support from a stent member. Instead, unsupported edge portion 54 is comprised of tubular membrane 30 without supplemental support from a stent member. Unsupported edges may also be referred to herein as "free" edges, and the unsupported edge portions of the membrane may be referred to herein as "flaps" or "tails." Unsupported edge portion 54 is relatively flaccid and compliant as compared to the supported edge portion 52. That is, unsupported edge portion 54 exhibits the flexibility and compliance of the unsupported tubular membrane 30, and therefore unsupported edge portion 54 may provide relatively little resistance to being deflected in an inward radial direction, for example.

The resistance of the unsupported edge portions to deflection, or flexibility, can be engineered by manipulating one or more stent graft design parameters. For example, design parameters such as the material composition of the membrane, the thickness of the membrane, the length of the segment, the diameter of the segment, the number of axial reinforcement members, the length of the stent members, the flexibility of the stent members, and the like, can have an effect on the flexibility of an unsupported edge portion. Those design parameters can be selected and established so as to create a stent graft with the desired characteristics for the flexibility of the unsupported edge portions. As will be described further below, the flexibility of the unsupported edge portions is a feature that facilitates or regulates radial flow between the exterior and interior of the stent graft, e.g., the flow that occurs between a side branch and primary conduit where a stent graft is placed.

Still referring to FIG. 1A, unsupported edge portion 54 of segment 40 is nested within the supported edge portion 56 of segment 42. Since unsupported edge portion 54 is relatively flaccid, whereas supported edge portion 56 is more rigid, a fluid flow path or channel exists between the unsupported edge portion 54 and the supported edge portion 56. The configuration of example stent graft 10 facilitates radial flow in the direction from the exterior of the stent graft 10 to the interior of the stent graft 10, as represented by flow arrows 60. In general, the fluid flow path may exist generally around the circumference of the device, for example in the overlap areas between the one or more axial reinforcement members 50. In some embodiments, when the fluid pressure at the exterior of the stent graft 10 is higher than the fluid pressure within the interior of the stent graft 10, the pressure differential can cause the unsupported edge portion 54 to be deflected in an inward radial direction, while the supported edge portion 56 remains substantially stationary. In that case, fluid flow can occur in a flow channel 70 between the outer periphery of unsupported edge portion 54 and the inner periphery of supported edge portion 56. Such flow can be directed from the exterior of the stent graft 10 to the interior of stent graft 10. Such flow can be described as inward radial flow through a flow channel 70 within the peripheral wall of stent graft 10. In some embodiments, inward radial flow can occur through the flow channels 70 existing between each of the adjacent segments of the stent graft device 10. The amount of differential pressure required to induce deflection of the unsupported edge 54 can depend upon various stent graft design parameters, as described above. In some embodiments, the unsupported edge 54 can be optimized to inhibit outward radial flow. For example, the amount that an unsupported edge overlaps a supported edge can be selected to inhibit outward radial flow.

While in some implementations the stent graft device is implanted to remain indefinitely, in some implementations it is desirable to implant the stent graft for a temporary period of time. For example, in some applications, it is desirable to implant a stent graft for a period of about one (1) year to remodel a conduit, and then to remove the stent graft. For example, as described further below, treatment of chronic pancreatitis or intrahepatic strictures using a stent graft are applications for which it is desirable to implant a stent graft for a finite period of time. In some applications, the desired finite period of time can be more than or less than one (1) year. In some cases, the clinician implanting the stent graft may not have a pre-conceived period of time that the stent graft is intended to be implanted.

For implementations where the stent graft is to be later removed, it may in some embodiments be desirable to configure the stent graft to inhibit or reduce tissue encapsulation of the device, including inhibition or reduction of tissue ingrowth, tissue bridging, and/or endothelialization. Inhibition of encapsulation can help facilitate the removal process. One of the design parameters of the stent grafts provided herein that can affect tissue encapsulation is the configuration of the flow channels 70 that exist between the supported edge portions and the unsupported edge portions of the membranous covering. Minimizing or inhibiting tissue encapsulation may be desirable as well to minimize a risk of occlusion or blockage of a fluid flow path 70 caused by excess tissue ingrowth, whether or not the device is intended to be later removed.

In general, openings in the wall of traditional stent grafts can have the potential, in some scenarios, to allow tissue encapsulation. To understand this better, consider bare metal stents as an example. Bare metal stents (stents with substantial wall openings because of having no membranous covering) are, in some cases, generally associated with substantial epithelial hyperplasia and endothelialization. Bare metal stents can allow tissue to grow and engulf or entangle portions of the bare stent framework, in some cases. That propensity for tissue encapsulation is at least partially attributable to the fact that tissue has little distance to travel to bridge the bare stent's frame members, i.e., to engulf portions of the stent frame.

The flow channels 70 of the stent graft devices provided herein can be configured to inhibit or reduce tissue encapsulation, despite providing openings in the wall of the stent graft to permit fluid flow. For example, in some embodiments, configuring flow channels that are longer, rather than shorter, can inhibit or reduce tissue encapsulation because longer flow channels may require tissue to grow a greater distance to engulf a stent graft device. The size of the flow channel openings can also be configured to inhibit or reduce tissue encapsulation of the stent graft devices provided herein. For instance, the use of smaller openings rather than larger openings may inhibit or reduce tissue encapsulation. In some embodiments, the use of membranous materials with a known low foreign body response (e.g., ePTFE) can also inhibit or reduce tissue encapsulation.

In some embodiments, the lengths of the flow channels 70 of the stent grafts provided herein are established by the distance that the adjacent segments nest or overlap with each other. That is, the unsupported edge portions of a segment (or a wind, in reference to FIGS. 2A and 2B, described below) can be configured to overlap the supported edge portions of the adjacent segment by a particular distance. For example, in example stent graft 10, the edge of unsupported edge portion 54 of segment 40 extends just beyond the stent member 22 of segment 42. The distance that the unsupported edge portion overlaps with an adjacent segment can be configured to be any suitable distance. For example, in some embodiments, the edge of the unsupported edge portion extends beyond the stent member of the adjacent segment. In some embodiments, the edge of the unsupported edge portion extends to about the farthest end of the stent member of the adjacent segment. In some embodiments, the unsupported edge extends to a distance between the ends of the stent member of the adjacent segment.

Figure 1B:
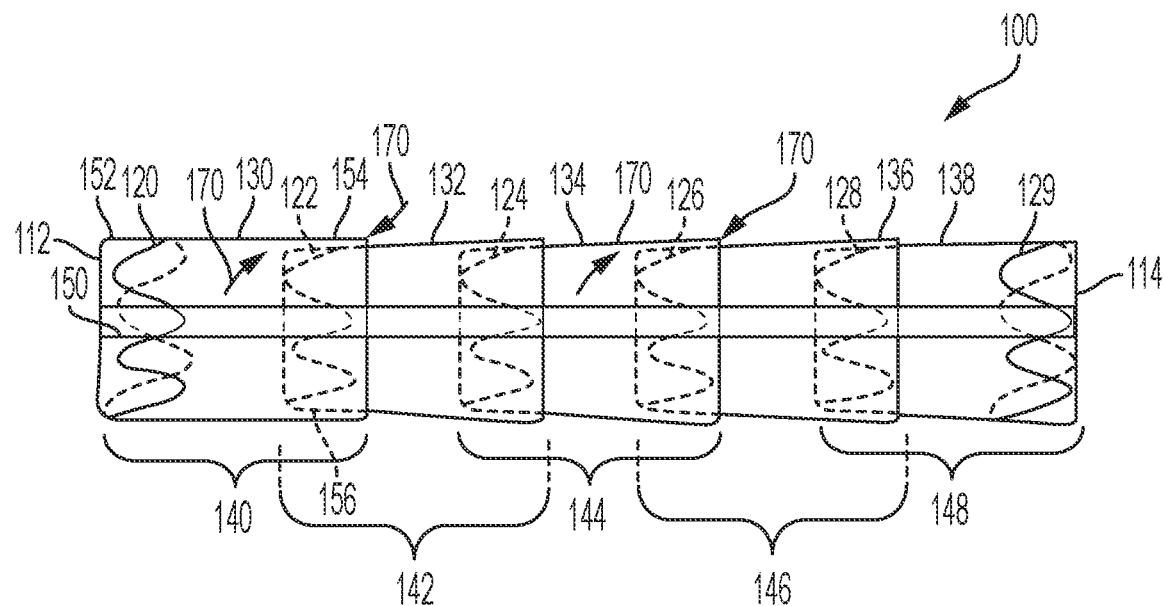

With reference to FIG. 1B, an example stent graft device 100 includes multiple tubular segments 140, 142, 144, 146, and 148. Each tubular segment 140, 142, 144, 146, and 148 includes at least one individual annular stent member 120, 122, 124, 126, 128 and 129, respectively, and a tubular membrane 130, 132, 134, 136, and 138, respectively. Unique end segment 148 includes two (2) annular stent members 128 and 129.

Adjacent segments of the tubular segments 140, 142, 144, 146, and 148 are partially nested within each other and are connected to one another by one or more axial reinforcement members 150. While example stent graft 100 is composed of five (5) segments 140, 142, 144, 146, and 148, some embodiments have fewer than five (5) segments (e.g., four (4), three (3), or two (2)). Some embodiments have more than five (5) segments (e.g., six (6), seven (7), eight (8), nine (9), ten (10), or more). Stent grafts having any appropriate number of segments are envisioned within the scope of this document.

Stent graft 100 includes a first end 112 and a second end 114. Connecting the first end 112 and the second end 114 is a substantially cylindrical tunnel. The peripheral wall of the tunnel is defined by the annular stents 120, 122, 124, 126, 128, and 129, and the tubular membranes 130, 132, 134, 136, and 138. Stent graft 100 is configured to conduct axial fluid flow within the tunnel (or lumen) between the first end 112 and the second end 114, in either direction.

Stent graft device 100 is also configured to facilitate flow through flow channels 170 at the peripheral wall of stent graft device 100 from the interior to the exterior of the stent graft device 100. Said differently, stent graft device 100 is configured to facilitate outward radial flow. The radial flow capability of stent graft 100 can, for example, facilitate flow between a primary conduit containing the stent graft 100 and one or more side branches or ducts with anastomoses intersecting with the conduit containing stent graft 100. In some embodiments, the flow channels 170 at the peripheral wall can be optimized to inhibit inward radial flow. For example, the amount that an unsupported edge overlaps a supported edge can be selected to inhibit inward radial flow.

Stent graft 100 includes one or more axial reinforcement members 150. Axial reinforcement members 150 link segments 140, 142, 144, 146, and 148 together, and assist in defining the desired spacing between the segments. Axial reinforcement members 150 define the overall length of example stent graft device 100.

Tubular membranes 130, 132, 134, 136, and 138 are comprised of a membranous material as described above in reference to tubular membranes 30, 32, 34, 36, and 38 of example stent graft 10.

In some embodiments, stent members 120, 122, 124, 126, 128, and 129 of example stent graft 100 are equivalent to stent members 20, 22, 24, 26, and 28, as described above in reference to example stent graft 10. Each segment, 140, 142, 144, 146, and 148 includes at least one individual stent member 120, 122, 124, 126, and 128, respectively. End segment 148 includes two (2) annular stent members 128 and 129.

With the exception of end segment 148, which serves as a unique end segment, the stent members 120, 122, 124, and 126 are located asymmetrically in relation to the segmented tubular membranes 130, 132, 134, and 136. That is, stent members 120, 122, 124, and 126 are located off-center and nearer to one of the edges of their respective membranes 130, 132, 134, and 136. As a result of the asymmetrical location of the stent members 120, 122, 124, and 126, one edge portion of each membrane 130, 132, 134, and 136 is supported by a stent member, while the other edge portion of each membrane 130, 132, 134, and 136 is not supported by a stent member. Therefore, one edge portion of each segment 140, 142, 144, and 146 is supported by a stent member, but the other edge portion of each segment 140, 142, 144, and 146 is unsupported and relatively flaccid, compared to the supported edge portion.

Segment 140 can be used to illustrate the previous point. Segment 140 includes a supported edge portion 152 and an unsupported edge portion 154. The supported edge portion 152 is supported by stent member 120, whereas the unsupported edge portion 154 has no such supplemental support from a stent member. Instead, unsupported edge portion 154 is comprised of tubular membrane 130 without supplemental support from a stent member. As such, unsupported edge portion 154 is relatively flaccid and compliant, as compared to the supported edge portion 152. That is, unsupported edge portion 154 exhibits the flexibility of the unsupported tubular membrane 130, and therefore unsupported edge portion 154 may provide relatively little resistance to being deflected in an outward radial direction.

The unsupported edge portion 154 of segment 140 is nested over the outer periphery of the supported edge portion 156 of segment 142. Since unsupported edge portion 154 is relatively flaccid, whereas supported edge portion 156 is more rigid, a fluid flow channel 170 exists between them. The configuration of example stent graft 100 can facilitate radial flow in the direction from the interior of the stent graft 100 to the exterior of the stent graft 100 through flow channels 170. In general, the fluid flow path may exist generally around the circumference of the device, for example in the overlap areas between the one or more axial reinforcement members 150. In some embodiments, when the fluid pressure within the interior of the stent graft 100 is higher than the fluid pressure at the exterior of the stent graft 100, the pressure differential can cause the unsupported edge portion 154 to be deflected in an outward radial direction, while the supported edge portion 156 remains substantially stationary. In that case, fluid flow can occur in a flow channel 170 between the inner periphery of unsupported edge portion 154 and the outer periphery of supported edge portion 156. Such flow is directed from the interior of the stent graft 100 to the exterior of stent graft 100, and can be described as outward radial flow through a flow channel within the peripheral wall of stent graft 100. Outward radial flow can occur through the flow channels 170 existing between each of the adjacent segments of the stent graft device 100, in some embodiments.

Figure 2A:
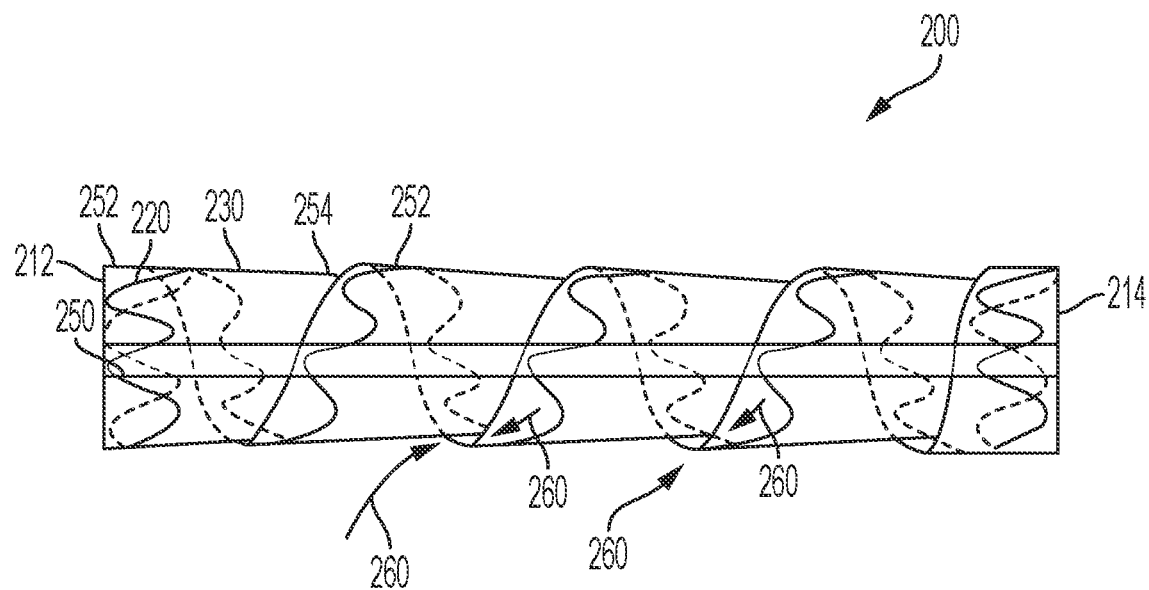
FIGS. 2A and 2B illustrate schematic side views of additional example embodiments of stent graft devices that can be deployed within a bodily conduit.

With reference to FIG. 2A, an example stent graft device 200 includes a continuous helical stent member 220, a continuous helical membranous covering 230, and one or more axial reinforcement members 250. The one or more axial reinforcement members 250 may be equivalent to the axial reinforcement members 50 and 150 described above in reference to FIGS. 1A and 1B.

Stent graft 200 includes a first end 212 and a second end 214. Between the first end 212 and the second end 214 is a substantially cylindrical tunnel. The peripheral wall of the tunnel is defined by the continuous helical stent member 220 and the continuous helical membranous covering 230. Stent graft 200 is configured to conduct fluid flow axially within the tunnel (or lumen) from the first end 212 toward the second end 214.

Stent graft device 200 is also configured to facilitate flow through flow channels 260 at the peripheral wall of stent graft device 200 from the exterior of the stent graft device 200 to the interior of the stent graft device 200. Said differently, stent graft device 200 is configured to facilitate inward radial flow. The radial flow capability of stent graft 200 can, for example, facilitate flow between one or more side branches or ducts with anastomoses intersecting with stent graft 200 and a primary conduit containing the stent graft 200.

In contrast to the stent graft devices 10 and 100 described above, the stent frame of example stent graft device 200 is not comprised of multiple individual annular stent rings. Rather, the stent frame of example stent graft device 200 is a single continuous helically wound or arranged stent member 220. The stent frame member of example stent graft device 200 is depicted as a single wire formed in a sinusoidal wave pattern, but any suitable configuration of a stent frame member is envisioned as within the scope of the devices discussed herein.

In contrast to the stent graft devices 10 and 100 described above, the membrane of example stent graft device 200 is not comprised of multiple individual tubular segments. Rather, the membrane of example stent graft device 200 is a continuous helically wound or arranged membranous covering 230. The continuous helical membranous covering 230 is wound or arranged in a helical configuration. For example, example stent graft device 200 has about five (5) winds. Stent grafts having any suitable number of winds are envisioned as within the scope of this document (e.g., two (2), three (2), four (4), six (6), seven (7), eight (8), nine (9), ten (10), or more).

The continuous helical stent member 220 and the continuous helical membranous covering 230 can be attached to each other as described above. In some embodiments, the continuous helical stent member 220 is attached so as to be approximately abutting an edge of the continuous helical membranous covering 230, i.e., in an asymmetrical manner. As a result of the asymmetrical placement of the continuous helical stent member 220 on the continuous helical membranous covering 230, one edge portion of the continuous helical membranous covering 230 is supported by a stent member but the other edge portion of continuous helical membranous covering 230 is unsupported by a stent member. For example, continuous helical membranous covering 230 includes a supported edge 252 and an unsupported edge 254. In order to keep FIG. 2A uncluttered and easier to understand, the literal edge of the unsupported edge 254 is not shown. The unsupported edge 254 of each wind is nested within the supported edge 252 of the adjacent wind. As described above in reference to example stent grafts 10 and 100, the overlap distance of the unsupported edge 254 with the supported edge 252 can be any suitable distance including beyond the edge of the stent member 220. Longer overlaps can tend to reduce the potential for endothelialization, tissue ingrowth, or tissue bridging in some implementations.

As described above, supported edge 252 may be relatively rigid, while unsupported edge 254 may be relatively flaccid. Since unsupported edge 254 is relatively flaccid, whereas supported edge 252 is more rigid, a fluid flow channel 260 exists between them. The configuration of example stent graft 200 can facilitate radial flow in the direction from the exterior of the stent graft 200 to the interior of the stent graft 200 through flow channels 260. In general, the fluid flow path may exist generally helically around the circumference of the device in the overlap areas, for example in the areas between the one or more axial reinforcement members 250. In some embodiments, when the fluid pressure at the exterior of the stent graft 200 is higher than the fluid pressure within the interior of the stent graft 200, the pressure differential causes the unsupported edge 254 to be deflected in an inward radial direction, while the supported edge 252 remains substantially stationary. In that case, fluid flow can occur in a flow channel 260 between the outer periphery of unsupported edge 254 and the inner periphery of supported edge 252. Such flow can be directed from the exterior of stent graft 200 to the interior of stent graft 200, and can be described as inward radial flow through a flow channel within the peripheral wall of stent graft 200. Inward radial flow can occur through the flow channels 260 existing between each of the adjacent winds of the stent graft device 200, in some embodiments.

Figure 2B:
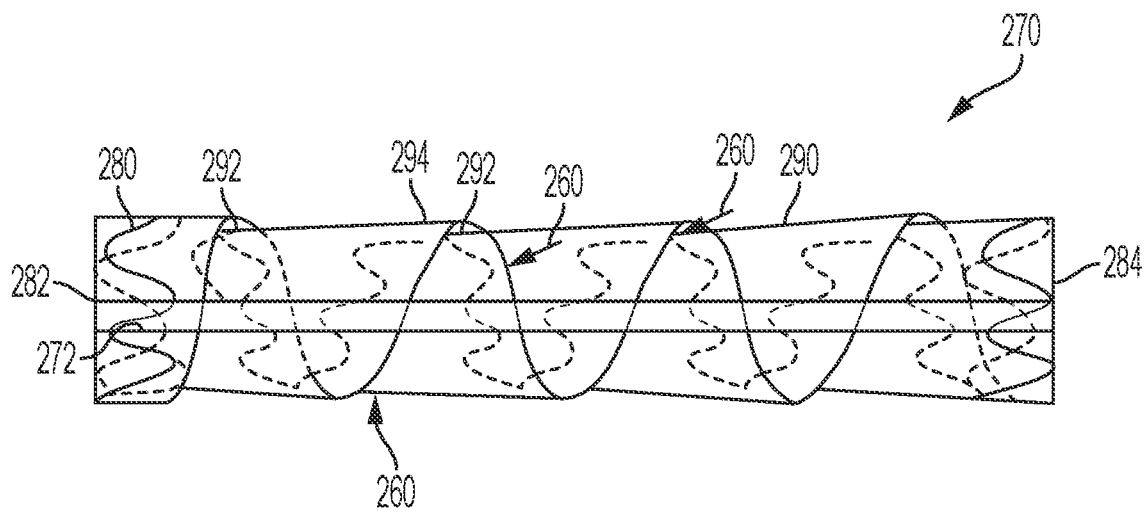

With reference to FIG. 2B, an example stent graft device 270 includes a continuous helical stent member 280, a continuous helical membranous covering 290, and one or more axial reinforcement members 272. The one or more axial reinforcement members 272 may be equivalent to the axial reinforcement members 50, 150, and 250 described above in reference to FIGS. 1A, 1B, and 2A.

Stent graft 270 includes a first end 282 and a second end 284. Between the first end 282 and the second end 284 is a substantially cylindrical tunnel. The peripheral wall of the tunnel is defined by the continuous helical stent member 280 and the continuous helical membranous covering 290. Stent graft 270 is configured to conduct fluid flow axially through the tunnel (or lumen) between the first end 282 and the second end 284, in either direction.

Stent graft device 270 is also configured to facilitate flow through flow channels 260 at the peripheral wall of stent graft device 270, from the interior of the stent graft device 270 to the exterior of the stent graft device 270. Said differently, stent graft device 270 is configured to facilitate outward radial flow. The radial flow capability of stent graft 270 can, for example, facilitate flow between a primary conduit containing the stent graft 270 and one or more side branches with anastomoses intersecting with stent graft 270.

In contrast to the stent graft devices 10 and 100 described above, the stent frame of example stent graft device 270 is not comprised of multiple individual annular stent rings. Rather, the stent frame of example stent graft device 270 is a single continuous helically wound or arranged stent member 280. The stent frame member of example stent graft device 270 is depicted as a single wire formed in a sinusoidal wave pattern, but any suitable configuration of a stent frame member can be incorporated.

In contrast to the stent graft devices 10 and 100 described above, the membrane of example stent graft device 270 is not comprised of multiple individual segments. Rather, the membrane of example stent graft device 270 is a continuous helically wound or arranged membranous covering 290. The continuous helically membranous covering 290 is wound or arranged in a helical configuration. For example, example stent graft device 270 has about five (5) winds. Stent grafts having any suitable number of winds are envisioned as within the scope of this document (e.g., two (2), three (2), four (4), six (6), seven (7), eight (8), nine (9), ten (10), or more).

The continuous helical stent member 280 and the continuous helical membranous covering 290 can be attached to each other as described above. In some embodiments, the continuous helical stent member 280 is attached so as to be approximately abutting an edge of the continuous helical membranous covering 290 in an asymmetrical manner. As a result of the asymmetrical placement of the continuous helical stent member 280 on the continuous helical membranous covering 290, one edge of the continuous helical membranous covering 290 is supported by a stent member but the other edge of continuous helical membranous covering 290 is unsupported by a stent member. For example, continuous helical membranous covering 290 includes a supported edge 292 and an unsupported edge 294. In order to keep FIG. 2B uncluttered and easier to understand, the literal edge of the supported edge 292 is not shown. The supported edge 292 of each wind is nested within the unsupported edge 294 of the adjacent wind. As described in reference to example stent grafts 10 and 100, the overlap distance of the unsupported edge 294 with the supported edge 292 can be any suitable distance, including beyond the edge of the stent member 280. Longer overlaps can tend to reduce the potential for endothelialization or tissue ingrowth, in some implementations.

As described above, supported edge 292 may be relatively rigid while unsupported edge 294 may be relatively flaccid. Since unsupported edge 294 is relatively flaccid, whereas supported edge 292 is more rigid, a fluid flow channel 260 exists between them. The configuration of example stent graft 270 facilitates radial flow in the direction from the interior of the stent graft 270 to the exterior of the stent graft 270 through glow channels 260. In general, the fluid flow path may exist generally helically around the circumference of the device in the overlap areas, for example in the areas between the one or more axial reinforcement members 272. In some embodiments, when the fluid pressure in the interior of the stent graft 270 is higher than the fluid pressure at the exterior of the stent graft 270, the pressure differential causes the unsupported edge 294 to be deflected in an outward radial direction, while the supported edge 292 remains substantially stationary. In that case, fluid flow can occur in a flow channel 260 between outer periphery of supported edge 292 and the inner periphery of unsupported edge 294. Such flow can be directed from the interior of the stent graft 270 to the exterior of stent graft 270, and can be described as outward radial flow through a flow channel 260 within the peripheral wall of stent graft 270. Outward radial flow can occur through the flow channels 260 existing between each of the adjacent winds of the stent graft device 270, in some embodiments.

Figure 3A:
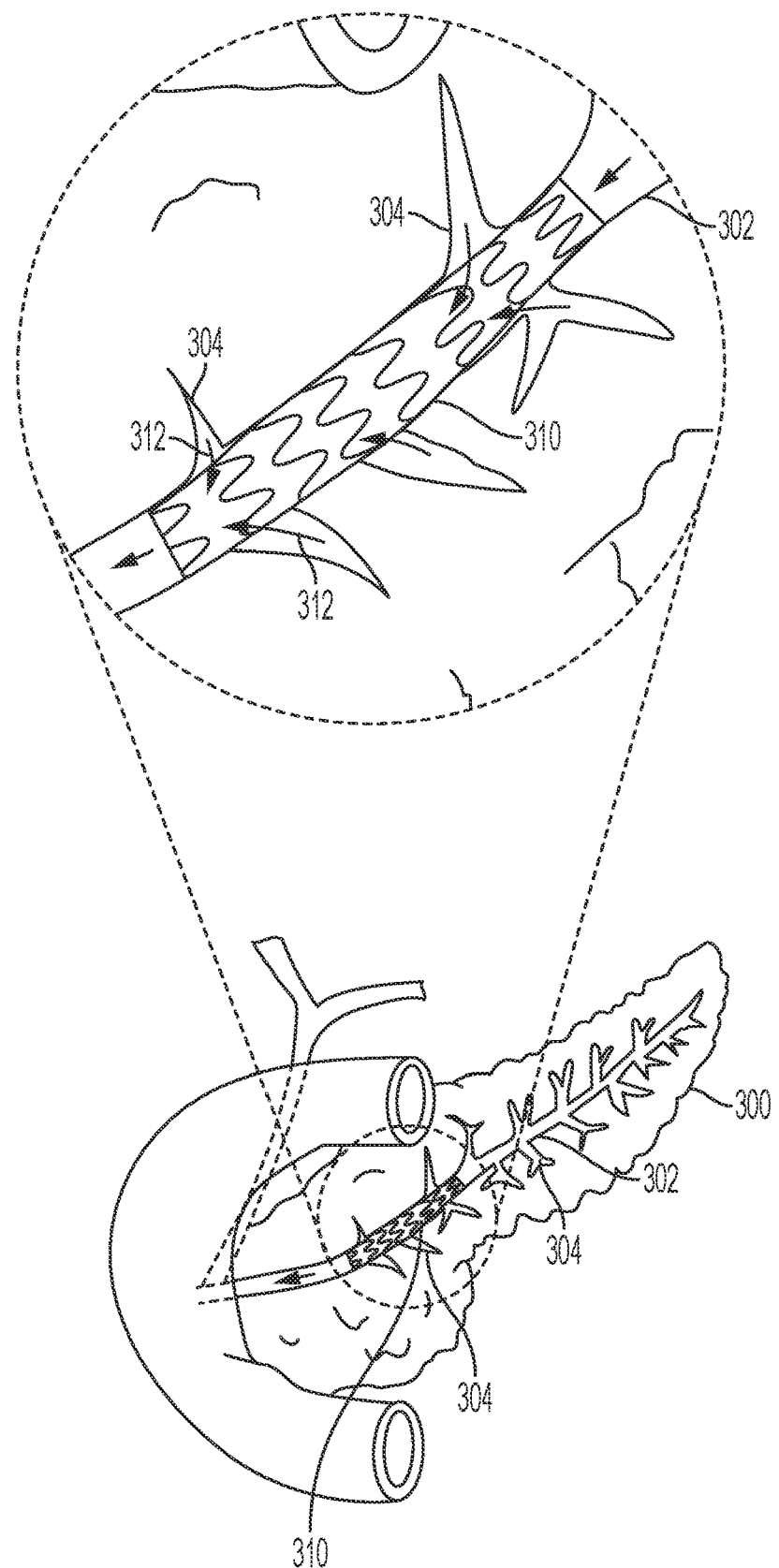
FIG. 3A illustrates a pancreas with an example intraluminal stent graft device deployed in the pancreatic duct.

With reference to FIG. 3A, a human pancreas 300 with an example intraluminal stent graft device 310 deployed in a main pancreatic duct 302 is depicted. The pancreatic ductal system includes, in addition to the main pancreatic duct 302, multiple side branches 304.

FIG. 3A depicts an example implementation of some embodiments of the stent graft devices provided herein. That is, some embodiments of the stent graft devices provided herein can be used as an interventional treatment for pancreatitis, i.e., to facilitate patency of the main pancreatic duct. In doing so, the stent graft devices provided herein can also facilitate flow of pancreatic enzymes and juices from the side branches 304 into the main pancreatic duct 302.

Pancreatitis can result when digestive enzymes generated in the pancreas are prevented, as by a stricture, from flowing through the pancreatic ductal system and into the duodenum portion of the small intestine. Pancreatic damage can occur as a result of cellular necrosis and apoptosis mechanisms that are triggered following activation of co-localized digestive enzymes before secretion from the pancreas. Blockage of the pancreatic ductal system can be a result of stones, fibrotic tissue, or other strictures in the main pancreatic duct.

Some embodiments of the stent grafts provided herein are suited to treating strictures in the main pancreatic duct. That is, the stent grafts provided herein can be implanted to open up a flow path through the main pancreatic duct. The stent grafts provided herein can also facilitate flow from side branches of the pancreatic ductal system into the main pancreatic duct. In addition, some embodiments of the stent grafts provided herein are suitable for later removal, and are resistive to endothelialization or tissue ingrowth. Such a feature can be beneficial because stents that are left in the main pancreatic duct can become occluded, for example, due to tissue encapsulation or clogging, thereby blocking flow and requiring removal.

The treatment of main pancreatic duct strictures due to chronic pancreatitis by deploying a stent graft in the main pancreatic duct can be a suitable implementation of stent graft embodiments that include radial inflow capability. As shown in the enlarged view, pancreatic enzymes flow from the side branches 304 into the main pancreatic duct 302, as depicted by arrows 312. Stent graft embodiments with radial inflow capability can facilitate the flow from the side branches 304 into the main pancreatic duct 302. For example, the stent graft embodiments 10 and 200, described above in reference to FIGS. 1A and 2A, include such radial inflow capability.

In some embodiments, the radial inflow or outflow capabilities of the stent grafts provided herein can exist along substantially the entire axial length of the stent graft device body. Such a feature can be desirable because the side branch anatomies of human patients can vary significantly, and the stent graft embodiments provided herein can thereby accommodate variation in side branch anatomies. That is, since radial inflow or outflow can occur along the entire axial length of the stent graft device body, it may generally not matter where the anastomoses of the side branches are in relation to the primary conduit, or in relation to particular portions of the stent graft device body. Hence, the stent graft devices provided herein may provide versatility for use in a wide variety of patients, without customization of the stent graft device to accommodate differing ductal system anatomies.

Figure 3B:
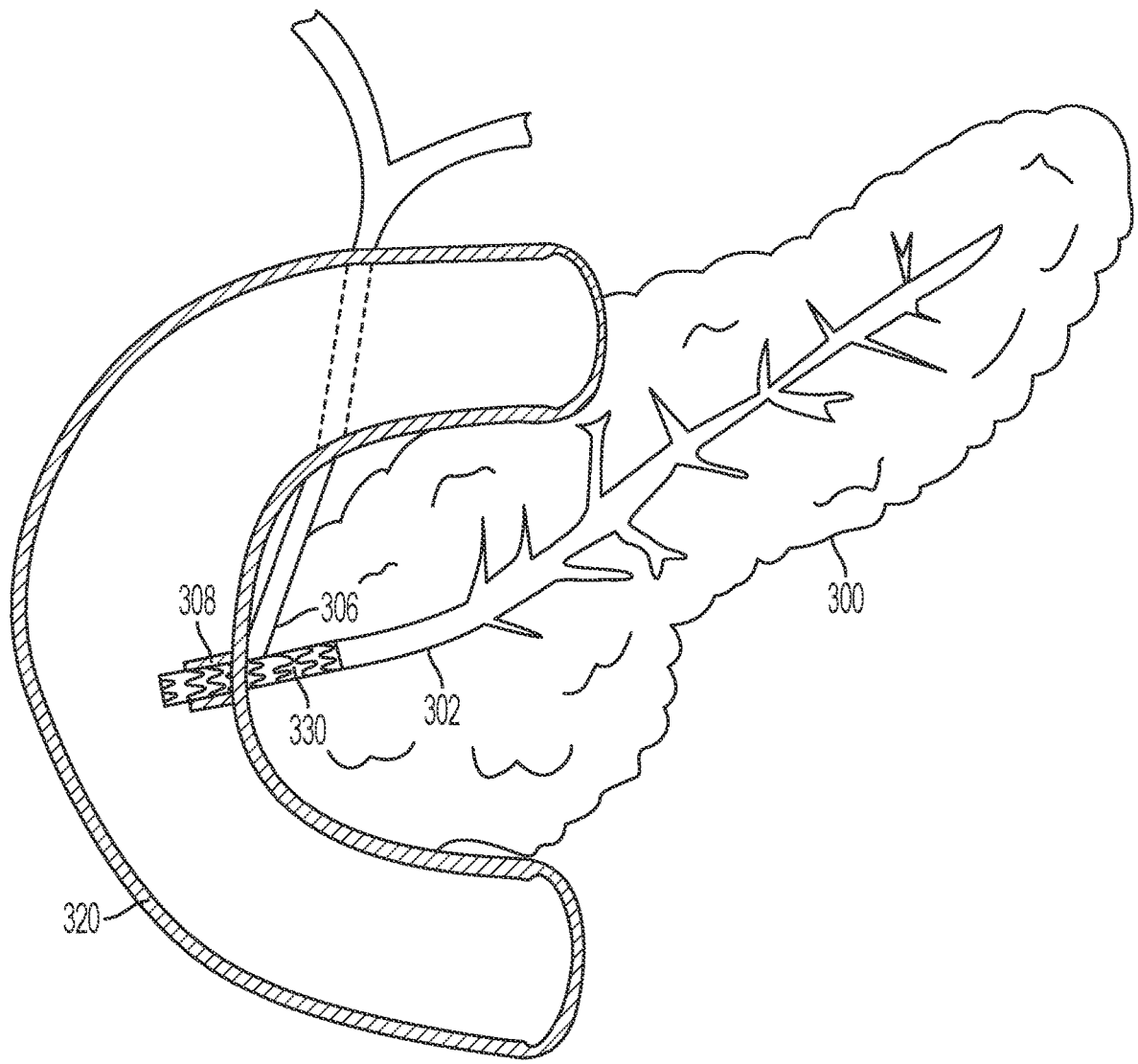
FIG. 3B illustrates a pancreas with an example intraluminal stent graft device deployed transpapillary and with sections in the pancreatic and common bile ducts.

With reference to FIG. 3B, a human pancreas 300 with an example intraluminal stent graft device 330 deployed in a main pancreatic duct 302 across the major papilla 308 and into the duodenal intestine 320 is depicted. FIG. 3B depicts another example implementation of some embodiments of the stent graft devices provided herein. That is, some embodiments of the stent graft devices provided herein can be used as an interventional treatment for strictures due to chronic pancreatitis, i.e., to facilitate patency of the major papilla and main pancreatic duct of the pancreas. In doing so, the stent graft devices provided herein can also facilitate radial inflow of bile from the common bile duct 306 into the main pancreatic duct 302. For example, stent graft embodiments 10 and 200 described above in reference to FIGS. 1A and 2A, which facilitate radial inflow, may be appropriate configurations for this implementation. In some implementations, it may be desirable for a portion of the stent graft 330 to protrude from the major papilla 308 into the duodenal intestine 320. In some implementations, some embodiments of the stent graft devices provided herein are deployed within the bile duct 306.

Figure 3C:
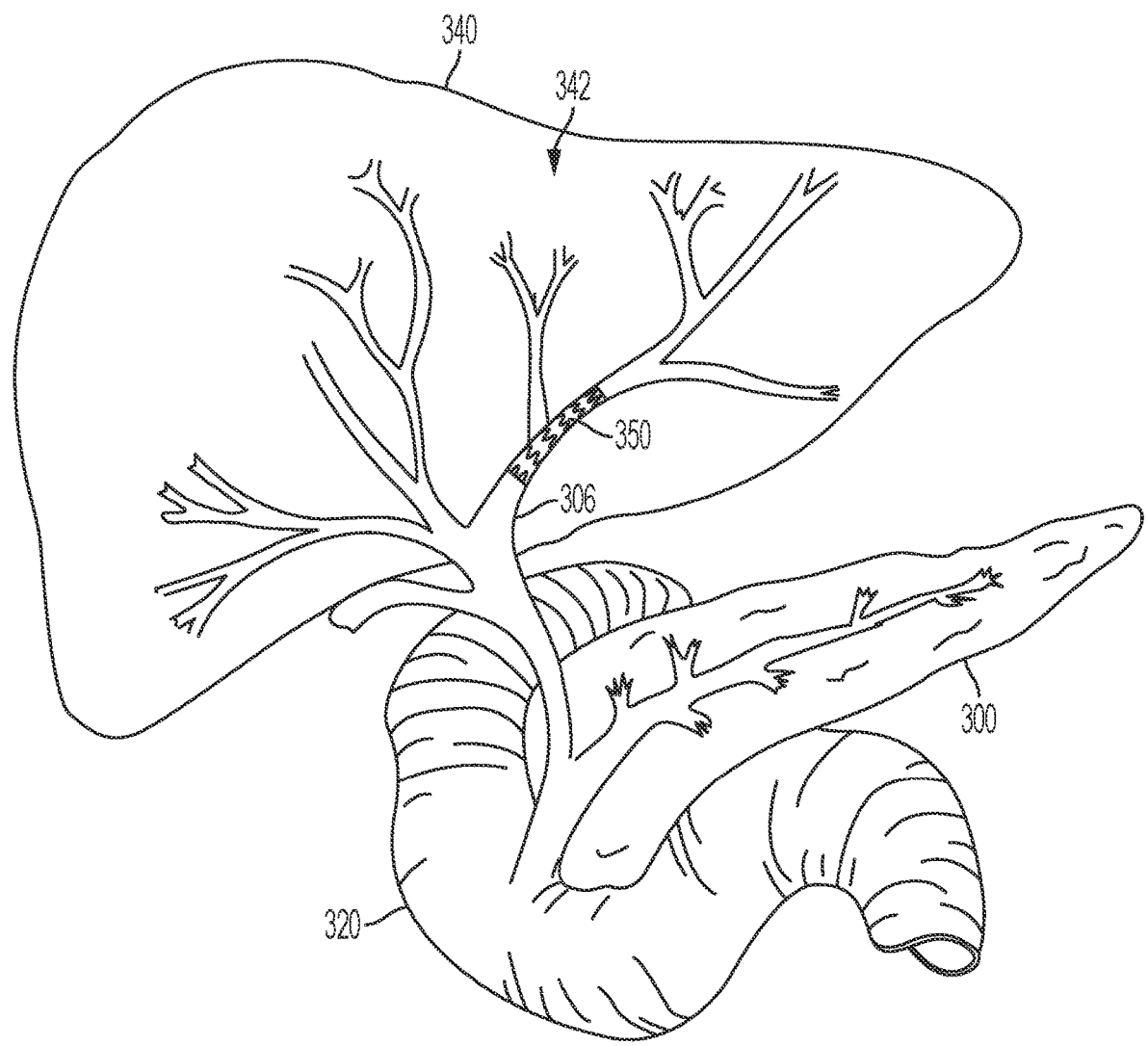
FIG. 3C illustrates a liver with an example intraluminal stent graft device deployed in the intrahepatic ductal system.
Figure 4:
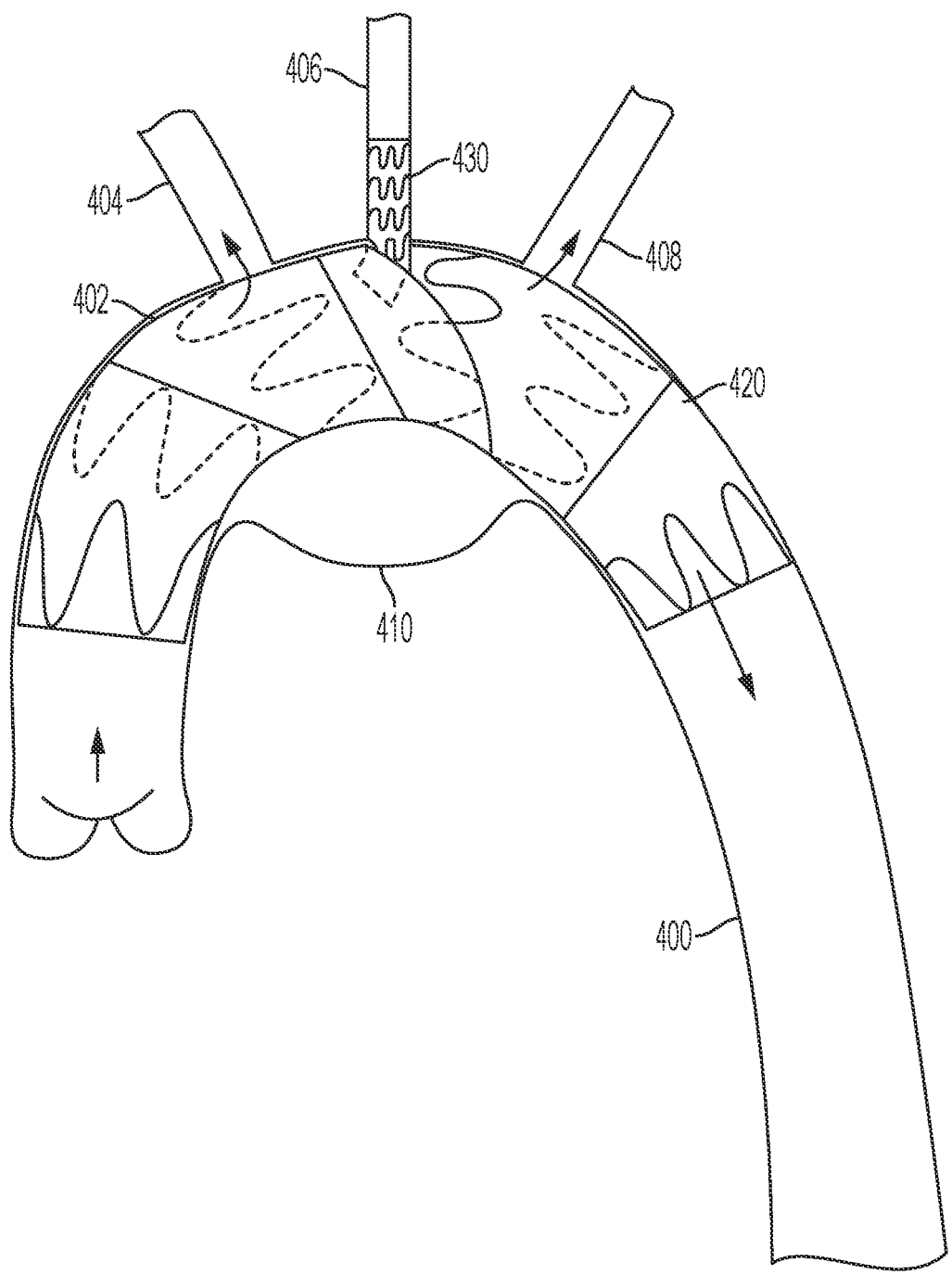
FIG. 4 illustrates a portion of an aorta with an example intraluminal stent graft device deployed within the aortic arch, and an example secondary stent graft device deployed within a branch artery.

With reference to FIG. 3C, a human liver 340 with an example intraluminal stent graft device 350 deployed in the intrahepatic ductal system 342 is depicted. Some embodiments of the stent graft devices provided herein can be used as an interventional treatment for intrahepatic biliary strictures, i.e., to facilitate patency of the common hepatic duct 306 and/or the intrahepatic ductal system 342 of the liver 340. In doing so, the stent graft devices provided herein can also facilitate radial inflow of bile from the intrahepatic ductal system 342 into the common hepatic duct 306. For example, stent graft embodiments 10 and 200 described above in reference to FIGS. 1A and 2A, which facilitate radial inflow, may be appropriate configurations for this implementation. With reference to FIG. 4, a portion of a human aorta 400 including an aortic arch 402 with an example intraluminal stent graft device 420 installed therein is depicted. The aortic arch 402 is depicted as having an aneurysm 410. This example implementation of the stent graft devices provided herein represents the treatment of an aneurysm in the wall of a vessel.

The aortic arch 402 has secondary arteries 404, 406, and 408 branching off from the aortic arch 402. An example secondary stent graft device 430 is depicted in the middle secondary artery 406. This illustrates the capability of some embodiments of the stent graft devices provided herein to allow one or more other devices to be deployed through or within the flow channels in the wall of the stent graft devices provided herein. In addition to using the flow channels to deploy a secondary stent 430, other usages are envisioned. For example, catheters can be routed through the flow channels to deploy other devices or to perform various treatments within or via the side branches.

In some implementations, it can be desirable to allow radial flow through some portions of the wall of the stent graft but not through other portions of the wall of the stent graft. For example, in reference to stent graft device 420, it may be desirable to allow radial flow through the wall to supply the secondary arteries 404, 406, and 408, but it may not be desirable to allow radial flow through the wall in the area of the aneurysm 410. Some embodiments of the stent graft devices provided herein can be configured to allow radial flow through portions of the stent graft wall while restricting radial flow through other portions of the stent graft wall. In some embodiments, this localized restricting capability can be created during device construction, or by the doctor just prior to implantation, or after deployment of the device. In some implementations, it is desirable to allow radial inflow through some portions of the wall of the stent graft, and to allow radial outflow through other portions of the wall. Some implementations of the stent graft devices provided herein can be configured to allow radial inflow through some portions of the wall of the stent graft, and to allow radial outflow through other portions of the wall.

Figure 5:
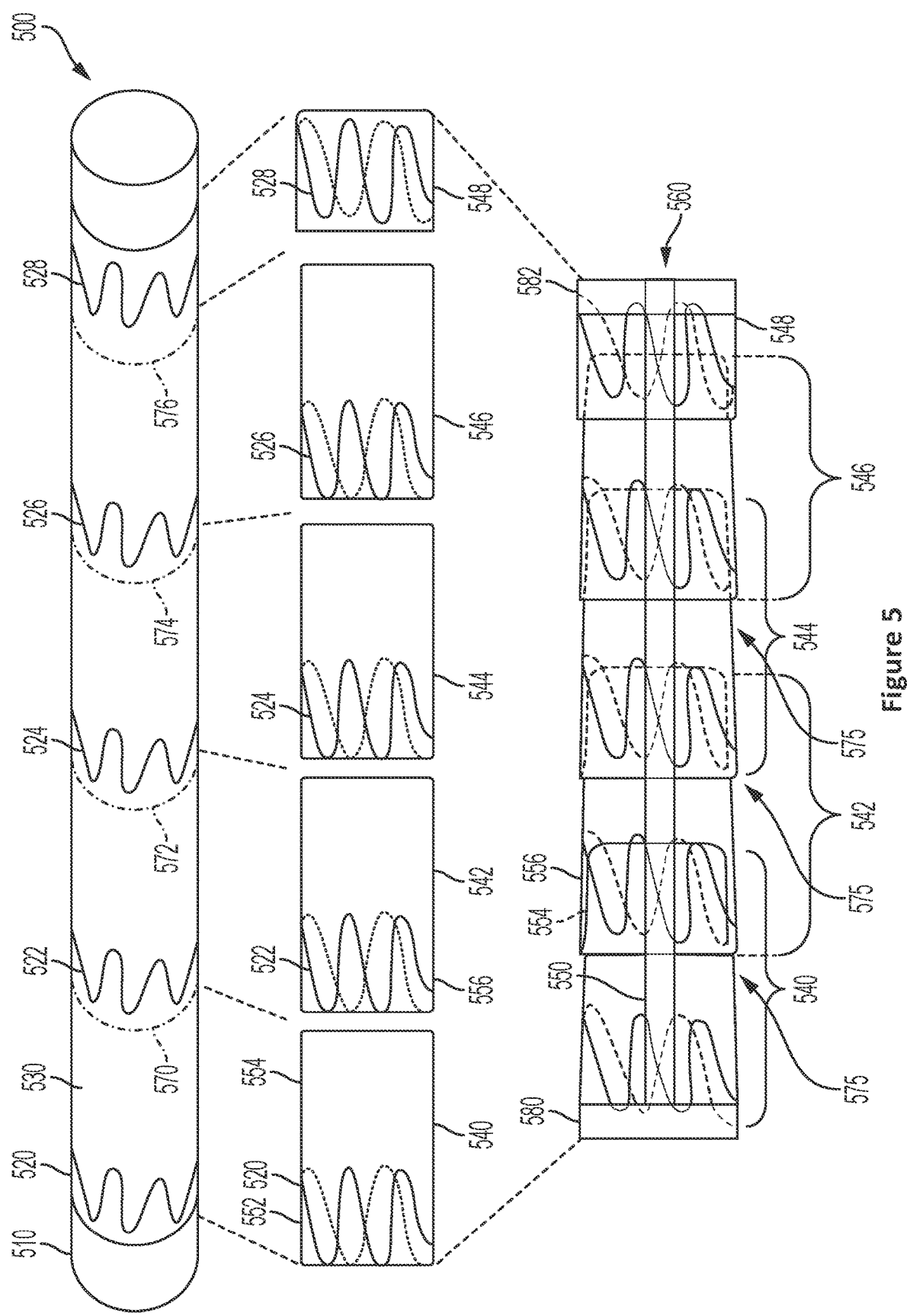
FIG. 5 is a schematic illustration of an example process for fabricating an intraluminal stent graft device.

With reference to FIG. 5, an exemplary process 500 for fabricating an intraluminal stent graft device 560 is schematically illustrated. The progressive steps of process 500 are illustrated generally, beginning with the view of the top of the sheet, continuing with the view in the middle, and ending with the finished stent graft 560 at the bottom of the sheet. Process 500 is provided as an exemplary process for fabricating an intraluminal stent graft device that has multiple discrete tubular segments such as stent graft embodiments 10 and 100, described above in reference to FIGS. 1A and 1B. However, other processes, sub-processes, and techniques for fabricating an intraluminal stent graft device with multiple discrete tubular segments are also envisioned within the scope of this document. Process 500 will be described as fabricating a stent graft device 560 from certain exemplary types of materials. However, the use of other types of materials to fabricate stent graft devices with multiple discrete tubular segments is also envisioned within the scope of this document. Although an intraluminal stent graft device with five (5) segments is used to illustrate process 500, a stent graft device with virtually any number of tubular segments can be fabricated using process 500.

As shown in the view at the top of FIG. 5, a membrane 530 with a plurality of attached stent members 520, 522, 524, 526, and 528 is formed to surround a cylindrical mandrel 510. The mandrel 510 is used as a form from which to build up a stent graft 560. The mandrel 510 can be comprised of any suitable mandrel material, e.g., stainless steel, tool steel, or aluminum. The diameter of mandrel 510 substantially determines the inner diameter of the stent graft 560. As such, an appropriately sized mandrel 510 should be selected in accordance with the size of the stent graft desired. For example, a smaller diameter mandrel should be used to form a small stent graft for a pancreatic duct implementation, as compared to a larger diameter mandrel for forming a larger stent graft for an aortic arch implementation. The length of mandrel 510 will be at least as long as the desired length of the stent graft to be fabricated, and the mandrel 510 may be substantially longer than the stent graft to be fabricated.

In some embodiments of process 500, a cushion tube (not shown) is included as a liner over the mandrel 510 surface. The cushion tube can be a suitable compressible material, e.g., an ePTFE tube or tape wrap. In some embodiments, a thin, heat resistant, non-stick liner made from a material such as a Kapton® is wrapped over the cushion tube.

A base layer of membrane 530 is wrapped around mandrel 510 over the cushion tube and non-stick liner. In some embodiments, a film-like, ePTFE membrane material is used. Other suitable materials, such as woven or knitted polyester, and the like, can also be used. In some embodiments, the ePTFE membrane 530 has a surface layer of fluorinated ethylene propylene (FEP) material on one side of the ePTFE membrane 530. The side of the membrane 530 with the FEP layer is oriented outward, i.e., away from the mandrel 510. FEP is a heat activated adhesive that, as described further below, can be used to bond layers of membrane. In some embodiments, the ePTFE membrane does not include a FEP layer. In such cases, a separate FEP film can be wrapped onto the ePTFE membrane.

In some embodiments, a second layer of ePTFE membrane 530 is wrapped onto the ePTFE and FEP already on the mandrel 510. In some embodiments, the second layer of ePTFE membrane 530 is a spiral wrap with about a fifty percent (50%) overlap. The second layer of ePTFE membrane 530 can also have a FEP layer on one side of the membrane 530. The side with the FEP layer should be oriented down onto the first layer of membrane 530, i.e., no FEP should be exposed in the area of the channel flaps after the addition of the second layer of ePTFE membrane 530. In some embodiments, the first two (2) layers of ePTFE membrane 530 make up the base membrane 530. In some embodiments, other constructions can make up the base membrane. For example, in some embodiments, more than two (2) layers of ePTFE membrane are included. In some embodiments, only one (1) layer of ePTFE membrane is included.

Stent members 520, 522, 524, 526, and 528 are added on top of the layers of membrane 530. In this embodiment, ring-like annular stent members are used. In some embodiments, stent members are wrapped around the membrane in another configuration, such as helically as described below in reference to FIG. 6. The annular stent members 520, 522, 524, 526, and 528 are to be placed on the mandrel 510 at locations in relation to the membrane 530 such that the desired axial lengths of the unsupported membrane (the flap length) will be created.

In some embodiments, a layer of ePTFE with FEP (oriented downward) is added over the stent members 520, 522, 524, 526, and 528. In some embodiments, this additional ePTFE is only wrapped over the individual stent members 520, 522, 524, 526, and 528, and is not wrapped over the entire length of the membrane 530. That is, each discrete stent member 520, 522, 524, 526, and 528 can be wrapped individually by a strand of ePTFE with FEP. The strands of ePTFE with FEP can be a little wider than the individual stent members 520, 522, 524, 526, and 528, so that the stent members 520, 522, 524, 526, and 528 will be fully laminated within the membrane material. In some embodiments, the additional ePTFE is wrapped over the entire length of the membrane 530.

A hot iron or other heat source is applied to all areas of the strands of ePTFE with FEP that cover the stent members 520, 522, 524, 526, and 528. The hot iron can be used to trace around the stent members 520, 522, 524, 526, and 528. The hot iron, with a temperature of about 670-720° F., for example, will activate the FEP and cause the strands of ePTFE to bond to the stent members 520, 522, 524, 526, and 528 and to the base membrane 530. The use of the hot iron causes the stent members 520, 522, 524, 526, and 528 to become firmly laminated between the strands of ePTFE and the base membrane 530, such that substantially all portions of the stent members 520, 522, 524, 526, and 528 are covered by ePTFE material.

In some embodiments, the mandrel 510, membrane 530, and stent members 520, 522, 524, 526, and 528 are then heated in an oven to activate the FEP adhesive, e.g., the FEP between the first two layers of membrane 530. Any suitable time and temperature profile can be used. For example, in some embodiments of process 500, the heating takes place at about 320° C. for about twelve (12) minutes.

After heating, and subsequent cooling, the non-stick liner can be removed from the mandrel 510. The membrane 530 with the stent members 520, 522, 524, 526, and 528 can also be removed from the mandrel 510.

In some embodiments, the membrane 530 is circumferentially cut at lines 570, 572, 574, and 576 to create discrete cylindrical segments 540, 542, 544, 546, and 548. The cutting is performed so as to create discrete cylindrical segments 540, 542, 544, and 546 with stent members 520, 522, 524, and 526 that are asymmetrically located on the discrete cylindrical segments 540, 542, 544, and 546 (see middle view of FIG. 5). In this example, the end segment 548 is unique, and its stent member 528 may be located in a suitable location that is different than the other discrete cylindrical segments 540, 542, 544, and 546. The asymmetrical location of the stent members 520, 522, 524, and 526 causes the discrete cylindrical segments 540, 542, 544, and 546 to each have a supported edge portion and an unsupported edge portion (a flap or tail), as described above in reference to stent graft embodiments 10 and 100.

Segment 540 can be used to illustrate the previous point. Segment 540 includes a supported edge portion 552 and an unsupported edge portion 554. The supported edge portion 552 is supported by stent member 520, whereas the unsupported edge portion 554 has no such supplemental support from a stent member. Instead, unsupported edge portion 554 is comprised of tubular membrane 530 without supplemental support from a stent member.

The discrete cylindrical segments 540, 542, 544, 546, and 548 are then placed again on mandrel 510 (or on a different mandrel), in some examples with a cushion tube and non-stick liner, and configured in relation to each other (nested together) as desired. That is, the tails of cylindrical segments are placed interior of, or exterior of, the supported edge of an adjacent cylindrical segment. As shown in the bottom view of FIG. 5, in some embodiments, the tails are placed interior of the supported edge portion of an adjacent cylindrical segment. For example, the tail 554 of cylindrical segment 540 is located within the supported edge portion 556 of the adjacent cylindrical segment 542. In some embodiments, the tails are placed over the exterior of the supported edge portion of an adjacent cylindrical segment (see, e.g., stent graft 100 of FIG. 1B). In some embodiments, a combination of interior and exterior placements of the tails in relation to the supported edges of the adjacent cylindrical segments can be created. The configuration of the tails in relation to the adjacent cylindrical segment can effect whether that portion of the stent graft device is configured for inward radial flow or outward radial flow.

One or more axial reinforcement members 550 are attached to the nested cylindrical segments 540, 542, 544, 546, and 548. In some embodiments, the axial reinforcement members 550 are strips of ePTFE that have a FEP layer on one side. In such embodiments, the strips of ePTFE with a FEP layer are attached to the cylindrical segments 540, 542, 544, 546, and 548 by applying a hot iron on the surface of the ePTFE strip. The heat from the hot iron will activate the FEP to cause the ePTFE strip to adhere to the cylindrical segments 540, 542, 544, 546, and 548. The axial reinforcement members 550 can be of any suitable width. In some embodiments, the axial reinforcement members 550 are about ¼" wide. Any suitable number of axial reinforcement members 550 can be used. In some embodiments, one (1), two (2), three (3), or more than three (3) axial reinforcement members 550 are used.

In some embodiments, one or both of the ends of stent graft 560 are reinforced by the addition of circumferential end reinforcement members 580 and 582, for example. In some embodiments, the end reinforcement members 580 and 582 are strips of ePTFE that have a FEP layer on one side. In such embodiments, end reinforcement members 580 and 582 are attached to the end cylindrical segments 540 and 548 by applying a hot iron on the surface of the ePTFE strip. The heat from the hot iron, for example at a temperature of about 670-720° F., will activate the FEP to cause the ePTFE strip to adhere to the cylindrical segments 540 and 548. The end reinforcement members 580 and 582 can be of any suitable width. In some embodiments, the end reinforcement members 580 and 582 are about ¼" wide. In some embodiments the end reinforcement members 580 and 582 are wrapped about a single circumference around cylindrical segments 540 and 548. In some embodiments, two (2) or more wraps of end reinforcement members 580 and 582 are made around cylindrical segments 540 and 548.

The stent graft 560 on the mandrel 510 can then be heated in an oven to ensure all FEP adhesive has been activated. Any suitable time and temperature profile can be used. For example, in some embodiments of process 500, the heating can take place at about 320° C. for about twelve (12) minutes.

The non-stick liner and the stent graft 560 can then be removed from the mandrel 510. The flow channels 575 between the tails and the supported edges can be checked to ensure that the channels are operable to be opened as desired. If any flow channels 575 are adhered together they can be gently separated using an appropriate tool, e.g., one of the tips of a pair of tweezers.

Figure 6:
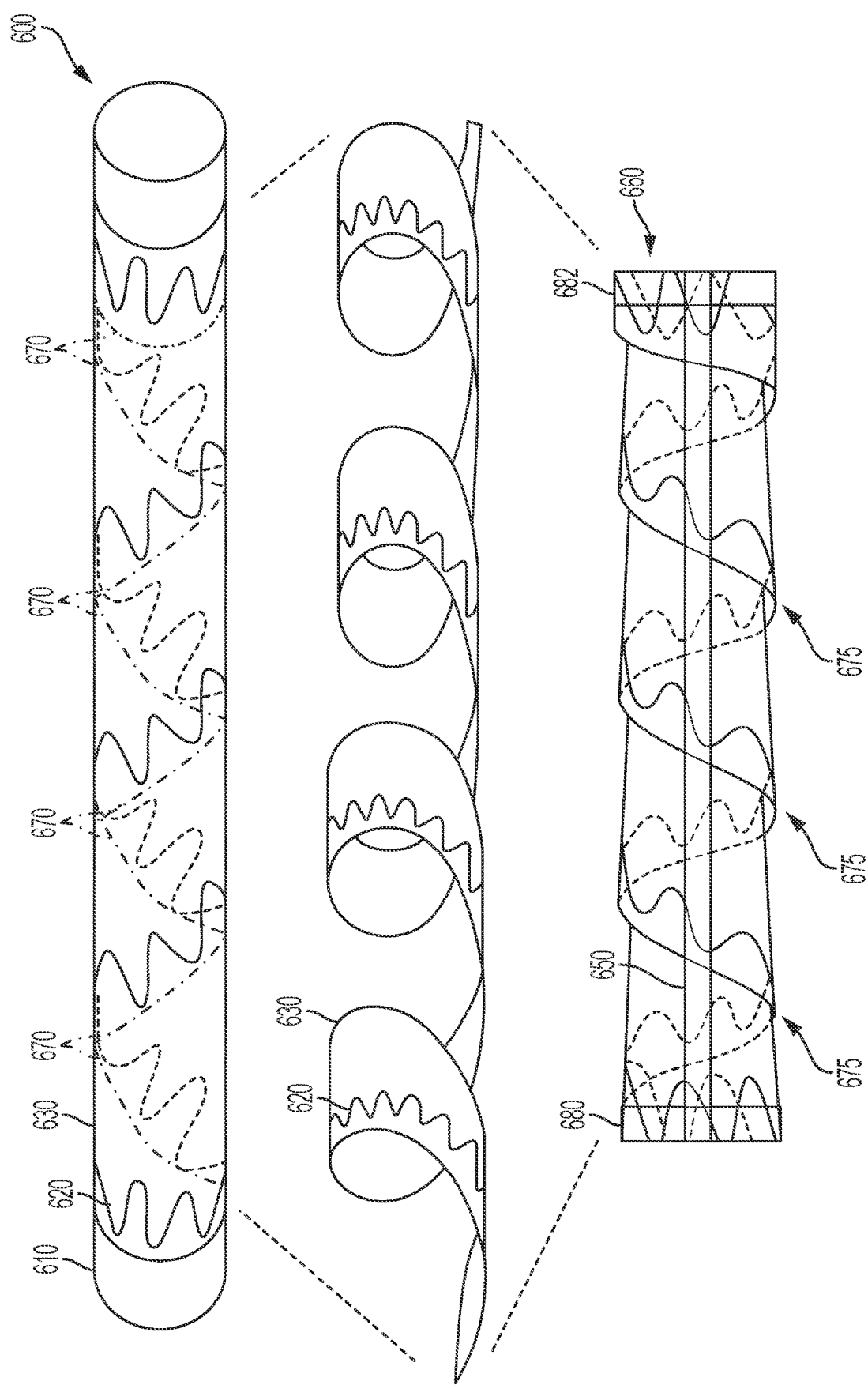
FIG. 6 is schematic illustration of another example process for fabricating an intraluminal stent graft device.

With reference to FIG. 6, an exemplary process 600 for fabricating an intraluminal stent graft device 660 is schematically illustrated. The progressive steps of process 600 are illustrated generally, beginning with the view of the top of the sheet, continuing with the view in the middle, and concluding with the finished stent graft 660 at the bottom of the sheet. Process 600 is provided as an example process for fabricating an intraluminal stent with a helically arranged membranous strip and a helically arranged support member attached to the helically arranged membranous strip, such as, for example, stent graft embodiments 200 and 270 as described above in reference to FIGS. 2A and 2B. The helically arranged membranous strip and the helically arranged support member are configured to comprise a plurality of turns or winds. However, other processes, sub-processes, and techniques for fabricating an intraluminal stent comprising a helically arranged membranous strip are also envisioned within the scope of this document. Process 600 will be described as fabricating a stent graft device 660 from certain exemplary types of materials. However, the use of other types of materials to fabricate stent graft devices with a helically arranged membranous strip is also envisioned within the scope of this document. Although an intraluminal stent graft device with five (5) turns (or winds) is used to describe process 600, a stent graft device with virtually any number of turns can be fabricated using process 600.

As shown in the view at the top of FIG. 6, a membrane 630 with a helically arranged support member 620 is formed to surround a cylindrical mandrel 610. The mandrel 610 is used as a form from which to build up a stent graft 660. The mandrel 610 can be comprised of any suitable mandrel material, e.g., stainless steel, tool steel or aluminum. For process 600, the diameter of mandrel 610 is oversized in comparison to the desired final inner diameter of the stent graft 660. For example, to fabricate a stent graft 660 with a final inner diameter of about ten (10) millimeters, a mandrel 610 with a diameter of about thirteen (13) millimeters can be used. As such, an appropriately oversized mandrel 610 should be selected in accordance with the final inner diameter of the stent graft 660 desired. The length of mandrel 610 will be longer than the desired length of the stent graft to be fabricated, and the mandrel 610 may be substantially longer than the stent graft to be fabricated.

In some embodiments of process 600, a cushion tube (not shown) is included as a liner over the mandrel 610 surface. The cushion tube can be a suitable compressible material, e.g., an ePTFE tube or tape wrap. In some embodiments, a thin, heat resistant, non-stick liner made from a material such as a Kapton® is wrapped over the cushion tube.

A base layer of membrane 630 is wrapped around mandrel 610 over the cushion tube and non-stick liner. In some embodiments, a film-like, ePTFE membrane material is used. Other suitable materials, such as woven or knitted polyester, and the like, can also be used. In some embodiments, the ePTFE membrane 630 has a surface layer of fluorinated ethylene propylene (FEP) material on one side of the ePTFE membrane. The side of the membrane 630 with the FEP layer is oriented outward, i.e., away from the mandrel 610. The FEP is a heat activated adhesive that, as described further below, can be used to bond layers of membrane. In some embodiments, the ePTFE membrane does not include a FEP layer. In such cases, a separate FEP film can be wrapped onto the ePTFE membrane.

In some embodiments, a second layer of ePTFE membrane 630 is wrapped onto the ePTFE and FEP already on the mandrel 610. In some embodiments, the second layer of ePTFE membrane 630 is spiral wrap with about a fifty percent (50%) overlap. The second layer of ePTFE membrane 630 can also have a FEP layer on one side of the membrane 630. The side with the FEP layer should be oriented down onto the first layer of membrane 630, i.e., no FEP should be exposed in the area of the channel flaps after the addition of the second layer of ePTFE membrane 630. In some embodiments, the first two (2) layers of ePTFE membrane 630 make up the base membrane 630. In some embodiments, other constructions can make up the base membrane. For example, in some embodiments, more than two (2) layers of ePTFE membrane are included. In some embodiments, only one (1) layer of ePTFE membrane is included.

Stent member 620 is added on top of the layers of membrane 630. In this exemplary embodiment, a single helically arranged stent member is used. The stent member 620 is helically wound on the mandrel 610 with a spacing between turns of stent members 620 that is greater than the desired spacing between the turns of stent members 620 in the final stent graft 660. For example, in some embodiments, a spacing of about ten (10) millimeters between the turns of stent members 620 is made on the mandrel 610, and a spacing of about two (2) millimeters between the turns of stent members 620 is made in the final product.

In some embodiments, a layer of ePTFE with FEP (oriented downward) is added over the stent member 620. In some embodiments, this additional ePTFE is only helically wrapped over the stent member 620, and is not wrapped over the entire length of the membrane 630. The strand of ePTFE with FEP may be a little wider than the stent member 620 so that the stent member 620 will be fully laminated within the membrane material. In some embodiments, the additional ePTFE is wrapped over the entire length of the membrane 630.

A hot iron or other heat source is applied to all areas of the strand of ePTFE with FEP that covers the stent members 620. The hot iron can be used to trace around the stent member 620. The hot iron, with a temperature of about 670-720° F., for example, will activate the FEP and cause the strand of ePTFE to bond to the stent member 620 and to the base membrane 630. The use of the hot iron causes the stent member 620 to become firmly laminated between the strand of ePTFE and the base membrane 630, such that substantially all portions of the stent member 620 are covered by ePTFE material.

In some embodiments, the mandrel 610, membrane 630, and stent member 620 are then heated in an oven to activate the FEP adhesive, e.g., the FEP between the first two layers of membrane 630. Any suitable time and temperature profile can be used. For example, in some embodiments of process 600, the heating takes place at about 320° C. for about twelve (12) minutes.

After heating, and subsequent cooling, the non-stick liner can be removed from the mandrel 610. The membrane 630 with the stent member 620 can also be removed from the mandrel 610.

In some embodiments, the membrane 630 is cut in a helical pattern along line 670. The cutting is performed so as to create a helical strip of membrane 630 with stent member 620 asymmetrically located on the helical strip of membrane 630 (see middle view of FIG. 6). The asymmetrical location of the stent member 620 will cause the final configuration of stent graft 660 to have a supported edge and an unsupported edge at each turn, as described above in reference to stent graft embodiments 200 and 270. That is, the helical strip of membrane 630 has lengthwise side regions (or margins), and one of the side regions is supported by stent member 620 while the other side region is unsupported.

The helical strip of membrane 630 with stent member 620 is then placed on an undersized mandrel, in some cases with a cushion tube and non-stick liner. For example, for a stent graft with about a ten (10) millimeter final inner diameter, a mandrel with about an eight (8) millimeter diameter can be used.

The turns of the helical strip of membrane 630 are then configured in relation to each other (nested together) as desired. That is, the unsupported side region (tails) of the turns are placed interior of, or the exterior of, the supported side region of adjacent turns. As shown in the bottom view of FIG. 6, in some embodiments, the tails are placed interior of the supported side region of an adjacent cylindrical segment. In some embodiments, the tails are placed over the exterior of the supported side region of an adjacent cylindrical segment (see, e.g., stent graft 270 of FIG. 2B). The configuration of the tails in relation to the adjacent cylindrical segment can effect whether that portion of the stent graft device is configured for inward radial flow or outward radial flow.

In some embodiments, one or more axial reinforcement members 650 are attached to the helical strip of membrane 630 with stent member 620. In some embodiments, the axial reinforcement members 650 are strips of ePTFE that have a FEP layer on one side. In such embodiments, the strips of ePTFE with a FEP layer are attached to the turns of the helical strip of membrane 630 with stent member 620 by applying a hot iron on the surface of the ePTFE strip. The heat from the hot iron will activate the FEP to cause the ePTFE strip to adhere to the helical strip of membrane 630 with stent member 620. The axial reinforcement members 650 can be of any suitable width. In some embodiments, the axial reinforcement members 650 are about Y4" wide. Any suitable number of axial reinforcement members 650 can be used. In some embodiments, one (1), two (2), three (3), or more than three (3) axial reinforcement members 650 are used.

In some embodiments, one or both of the ends of stent graft 660 are reinforced by the addition of circumferential end reinforcement members 680 and 682, for example. In some embodiments, the end reinforcement members 680 and 682 are strips of ePTFE that have a FEP layer on one side. In such embodiments, end reinforcement members 680 and 682 are attached to the ends of the helical strip of membrane 630 with stent member 620 by applying a hot iron on the surface of the ePTFE strip. The heat from the hot iron, for example at a temperature of about 670-720° F., will activate the FEP to cause the ePTFE strip to adhere to the membrane 630. The end reinforcement members 680 and 682 can be of any suitable width. In some embodiments, the end reinforcement members 680 and 682 are about Y4" wide. In some embodiments the end reinforcement members 680 and 682 are wrapped about a single circumference around membrane 630. In some embodiments, two (2) or more wraps of end reinforcement members 680 and 682 are made around the membrane 630.

The stent graft 660 on the mandrel can then be heated in an oven to ensure all FEP adhesive has been activated. Any suitable time and temperature profile can be used. For example, in some embodiments of process 600, the heating can take place at about 320° C. for about twelve (12) minutes.

The non-stick liner and the stent graft 660 can then be removed from the mandrel. The flow channels 675 between the tails and the supported edges can be checked to ensure that the channels 675 are operable to be opened as desired. If any flow channels 675 are adhered together they can be gently separated using an appropriate tool, e.g., one of the tips of a pair of tweezers.

Figure 7:
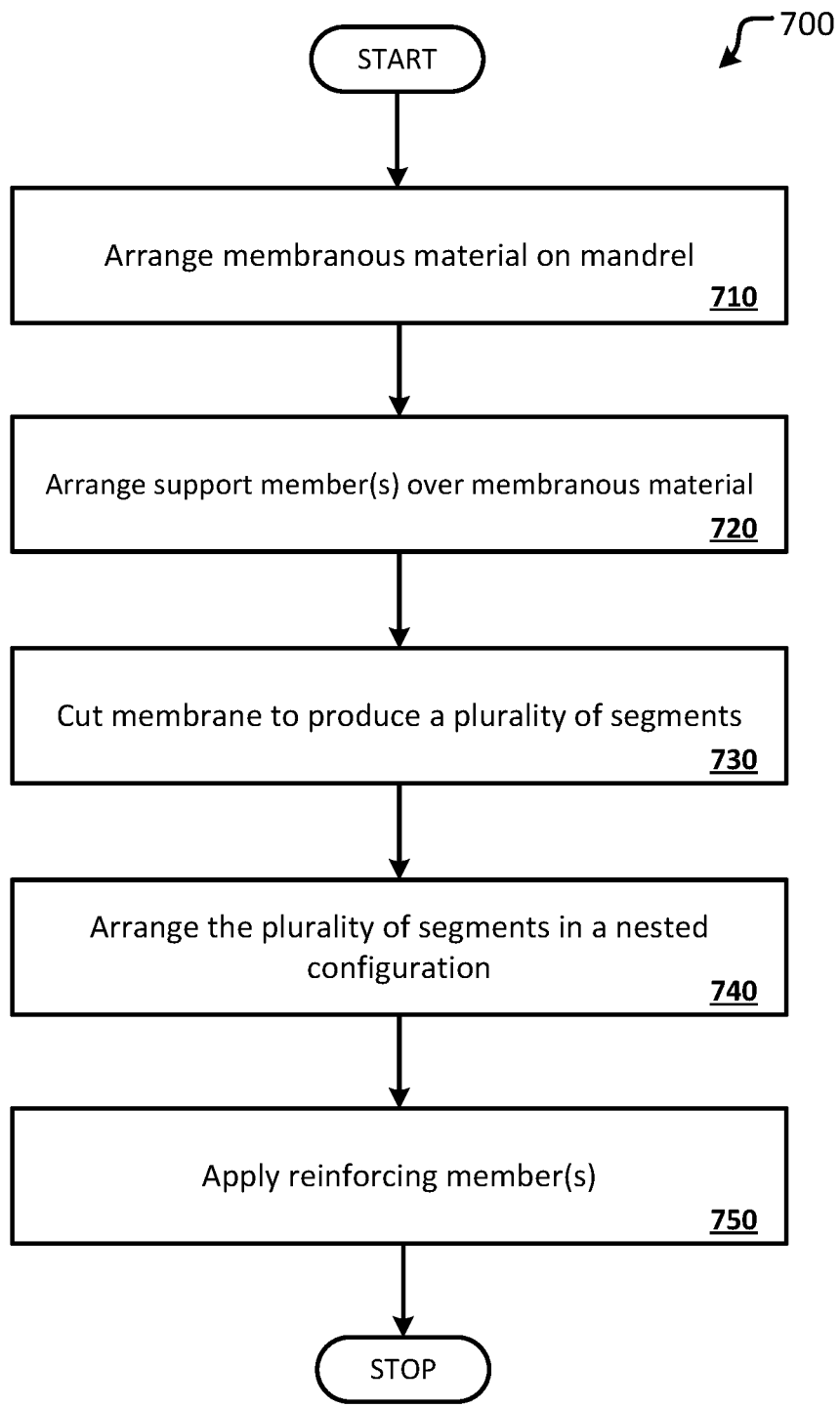
FIG. 7 depicts a flowchart of an example process for fabricating an intraluminal stent graft device.

FIG. 7 is a flowchart of an exemplary process 700 for fabricating a stent graft device with discrete cylindrical segments arranged in a nested configuration as provided herein. For example, process 700 can be used to fabricate stent graft embodiments 10 and 100 of FIGS. 1A and 1B. Process 700 also corresponds to some embodiments of the process depicted in FIG. 5, for example.

At operation 710, membranous material is arranged on a mandrel. The mandrel can be sized corresponding to an inner diameter of the stent graft to be fabricated. As described above, in some embodiments ePTFE is used for the membranous material. In some embodiments, a FEP layer is included on one surface of the ePTFE. In some embodiments, two (2) or more layers of film material comprise the membranous material as a laminate. In some embodiments, woven or knitted membranes are used.

At operation 720, a plurality of individual ring-like annular support members are arranged over the membranous material. In some embodiments, the individual ring-like annular support members are stent members. In some embodiments, the stent members are formed wires or laser cut lattice rings. The stent members are placed over the membranous material in locations that will result in the desired asymmetrical stent placement configuration as described above in reference to FIGS. 1A and 1B. Strips of membrane material can be placed over the support members and laminated to the membranous material so as to attach and laminate the stent members onto the membranous material. In some embodiments a hot iron can be used to adhere the strips of membrane material to the membranous material to thereby laminate the support members with membranous material.

In some embodiments, the mandrel with the partially completed stent graft device is then heated in an oven to activate the FEP. The activation of FEP bonds the layers of membranous material together.

At operation 730, after removing the partially completed stent graft from the mandrel, the base membrane can be cut to produce a plurality of cylindrical segments. The cuts are made in locations on the base membrane near the edges of stent members. The locations of the stent members are thereby located axially asymmetrical on the segments. That is, one edge of the cylindrical segments has support from a stent member but the other edge does not (it is the tail portion).

At operation 740 the plurality of cylindrical segments are again placed on the mandrel, or another mandrel, and arranged in a nested configuration in accordance with the type of stent graft device desired, such as a radial inflow stent graft device or a radial outflow stent graft device. If a radial inflow stent graft is desired, the tails of the cylindrical segments are placed interior of (i.e., closer to the mandrel) the supported edges of the adjacent cylindrical segments. If a radial outflow stent graft is desired, the tails of the cylindrical segments are placed exterior of (i.e., further from the mandrel) the supported edges of the adjacent cylindrical segments.

At operation 750, reinforcing members are applied to the cylindrical segments that are arranged in the nested configuration. One or more axial reinforcement members can be applied. In some embodiments, end reinforcement members can also be applied to one or both ends of the stent graft device. In some embodiments, the reinforcement members are strips of ePTFE membrane with a FEP layer. In some embodiments, the strips are about Y4" wide. The reinforcement members may be of any suitable width.

In some embodiments, the mandrel with the completed stent graft device is once again heated in an oven to activate the FEP. The activation of FEP bonds the layers of membranous material together to create a completed stent graft device.

Figure 8:
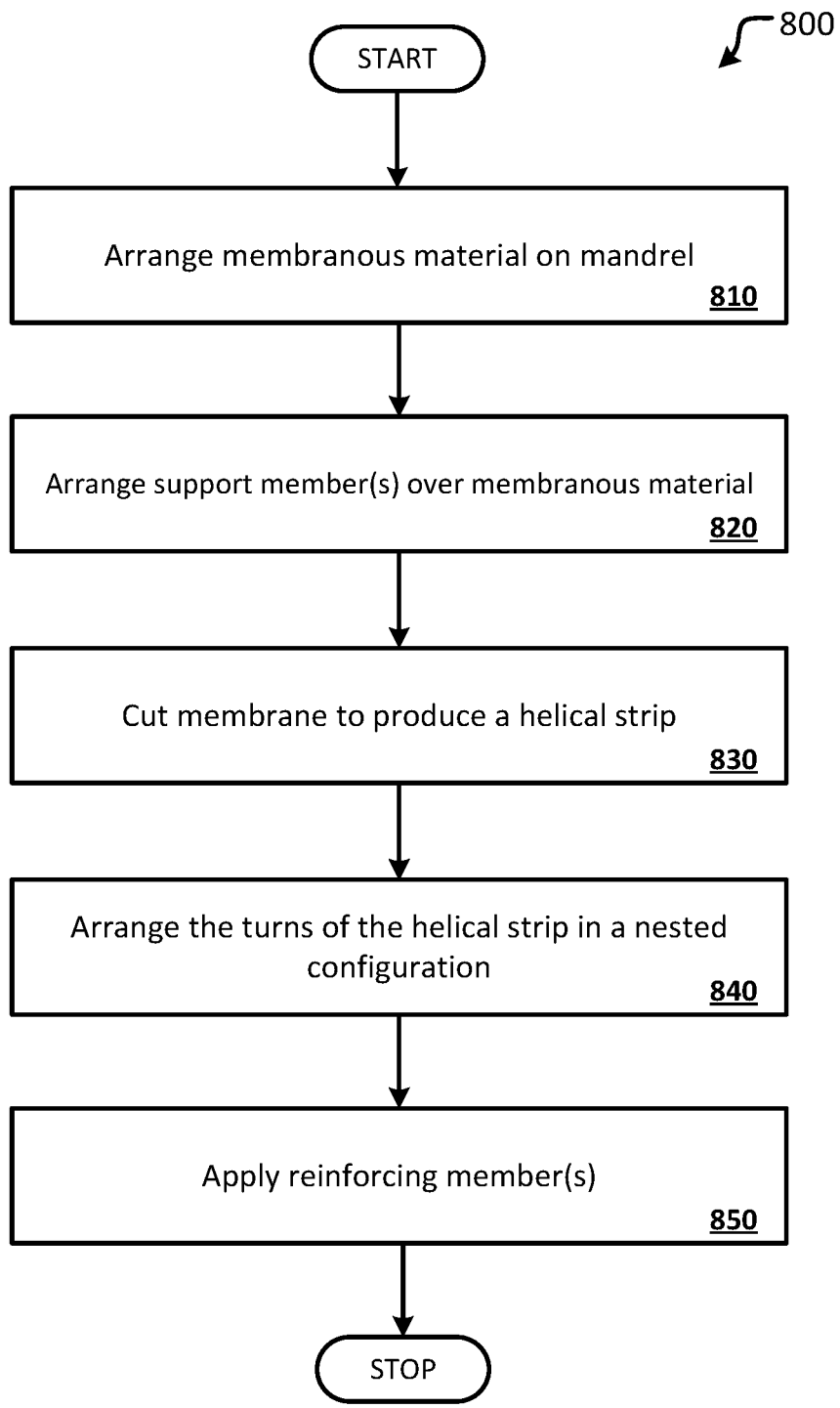
FIG. 8 depicts a flowchart of another example process for fabricating an intraluminal stent graft device.

FIG. 8 is a flowchart of an example process 800 for fabricating a stent graft device with a helically arranged membrane, wherein the turns of the helix overlap to create a nested configuration. For example, process 800 can be used to fabricate stent graft embodiments 200 and 270 of FIGS. 2A and 2B. Process 800 also corresponds to some embodiments of the process depicted in FIG. 6, for example.

At operation 810, membranous material is arranged on a mandrel. In some embodiments, the mandrel is over-sized for the inner diameter of the stent graft to be fabricated. For example, to fabricate a stent graft with a final inner diameter of about ten (10) millimeters, a mandrel with a diameter of about thirteen (13) millimeters can be selected. As described above, in some embodiments ePTFE is used for the membranous material. In some embodiments, a FEP layer is included on one surface of the ePTFE. In some embodiments, two (2) or more layers of film material can comprise the membranous material as a laminate. In some embodiments, woven or knitted membranes are used.

At operation 820, a single continuous support member is helically arranged over the membranous material. In some embodiments, the helically arranged support member is a stent member. In some embodiments, the stent member is made of a formed wire or a laser cut lattice strip. The stent member is placed over the membranous material in a location that will result in the desired asymmetrical stent placement configuration, as described above in reference to FIGS. 2A and 2B. A strip of membrane material can be placed over the support member and laminated to the base membrane, so as to attach and laminate the stent member within the membranous material. In some embodiments a hot iron can be used to adhere the strip of membranous material to the base material to thereby laminate the support member within membranous material.

In some embodiments, the mandrel with the partially completed stent graft device is then heated in an oven to activate the FEP. The activation of FEP bonds the layers of membrane material together.

At operation 830, after removing the partially completed stent graft from the mandrel, the base membrane can be cut to produce a helical strip of membranous material with an asymmetrically located support member. The helical cut is made on the base membrane near the edges of the stent member. The stent member is thereby located asymmetrically on the helical strip of membranous material.

At operation 840, in some embodiments, the plurality of cylindrical segments are placed on an undersized mandrel. For example, for a stent graft with about a ten (10) millimeter final inner diameter, a mandrel with about an eight (8) millimeter diameter can be used. The turns of the helical strip of membranous material are then arranged in a nested configuration in accordance with the type of stent graft device desired, such as a radial inflow stent graft device or a radial outflow stent graft device. If a radial inflow stent graft device is desired, the tails of the turns are placed interior of (i.e., closer to the mandrel) the supported edge of the adjacent turn. If a radial outflow stent graft is desired, the tails of the turns are placed exterior of (i.e., further from the mandrel) the supported edge of the adjacent turn.

At operation 850, reinforcing members are applied to the cylindrical segments that are arranged in the nested configuration. One or more axial reinforcement members can be applied. In some embodiments, end reinforcement members can be applied to one or both ends of the stent graft device. In some embodiments, the reinforcement members are strips of ePTFE membrane with a FEP layer. In some embodiments, the strips are about ¼" wide. The reinforcement members may be of any suitable width.

In some embodiments, the mandrel with the completed stent graft device is once again heated in an oven to activate the FEP. The activation of FEP bonds the layers of membrane material together to create a completed stent graft device.

While this specification contains many specific implementation details, these should not be construed as limitations on the scope of any devices, methods, and systems discussed herein, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Particular embodiments of the subject matter have been described. Other embodiments are within the scope of the following claims.

What is claimed is:

1. A method of treatment comprising:
   delivering a stent graft to a treatment site; and
   deploying the stent graft at the treatment site such that a first cylindrical segment and a second, adjacent cylindrical segment of the stent graft are in a nested configuration, and whereby fluid flow is facilitated through a fluid flow channel defined between an unsupported end portion of the first cylindrical segment and a supported end portion of the second, adjacent cylindrical segment, the first cylindrical segment and the second, adjacent cylindrical segment being fixedly attached to each other by an elongate axial reinforcement member.

2. The method of claim 1, further comprising facilitating an inward radial flow through the fluid flow channel to impede tissue ingrowth between the unsupported end portion and the supported end portion.

3. The method of claim 1, further comprising facilitating an outward radial flow through the fluid flow channel to impede tissue ingrowth between the unsupported end portion and the supported end portion.

4. The method of claim 1, further comprising deploying a secondary stent graft that is separate from the stent graft, the secondary stent graft fluidly coupled with the fluid flow channel.

5. The method of claim 4, further comprising routing a catheter through the fluid flow channel.

6. The method of claim 1, wherein delivering the stent graft to the treatment site includes maintaining a pressure differential between an interior of the stent graft and an exterior of the stent graft during delivery of the stent graft to the treatment site.

7. The method of claim 1, wherein the facilitating fluid flow through the fluid flow channel includes increasing a pressure differential between an interior of the stent graft and an exterior of the stent graft.

8. The method of claim 1, wherein the facilitating fluid flow through the fluid flow channel includes decreasing a fluid pressure within the interior of the stent graft with respect to a fluid pressure at an exterior of the stent graft.

9. The method of claim 1, wherein the facilitating fluid flow through the fluid flow channel includes deflecting the unsupported end portion in an inward radial direction to increase a separation between the supported end portion and the unsupported end portion.

10. The method of claim 9, further comprising: inhibiting fluid flow in an outward radial direction through the fluid flow channel during deflection of the unsupported end portion in the inward radial direction.

11. The method of claim 1, wherein the fluid flow channel is located around a circumference of the stent graft.

12. The method of claim 1, wherein the first cylindrical segment and the second, adjacent cylindrical segment are fixedly attached to each other by a plurality of elongate axial reinforcement members such that the fluid flow channel is defined between the plurality of elongate axial reinforcement members.

13. A method of treatment comprising:
delivering a stent graft to a treatment site while maintaining a pressure differential between an interior of the stent graft and an exterior of the stent graft during delivery of the stent graft to the treatment site; and
deploying the stent graft at the treatment site such that fluid flow is facilitated through a fluid flow channel between an unsupported end portion of a first cylindrical segment of the stent graft and a supported end portion of a second, adjacent cylindrical segment of the stent graft by increasing the pressure differential between the interior of the stent graft and the exterior of the stent graft.

14. The method of claim 13, wherein the facilitating fluid flow through the fluid flow channel comprises deflecting the unsupported end portion in an inward radial direction while the supported end portion remains substantially stationary.

15. The method of claim 14, further comprising inhibiting fluid flow in an outward radial direction through the fluid flow channel during deflection of the unsupported end portion in the inward radial direction.

16. The method of claim 13, further comprising deploying a secondary stent graft that is separate from the stent graft, the secondary stent graft fluidly coupled with the fluid flow channel.

17. The method of claim 16, further comprising routing a catheter through the fluid flow channel.

18. A method of treatment comprising:
delivering a stent graft to a treatment site; and
deploying the stent graft at the treatment site such that fluid flow is facilitated through a plurality of fluid flow channels of the stent graft, each of the plurality of fluid flow channels being located between an unsupported end portion of a first cylindrical segment of the stent graft and a supported end portion of a second, adjacent cylindrical segment of the stent graft, and in an overlap area between two of a plurality of elongate axial reinforcement members.

19. The method of claim 18, further comprising deploying a secondary stent graft separately from the stent graft, the secondary stent graft fluidly coupled with at least one of the plurality of fluid flow channels.

20. The method of claim 19, further comprising routing a catheter through one of the plurality of fluid flow channels.

* * * * *